US012656341B2

(12) United States Patent
Woell et al.

(10) Patent No.: US 12,656,341 B2
(45) Date of Patent: Jun. 16, 2026

(54) PROCESS FOR THE PREPARATION OF LIPIDATED PROTEINACEOUS STRUCTURES

(71) Applicant: MERCK PATENT GMBH, Darmstadt (DE)

(72) Inventors: Steffen Woell, Mainz (DE); Stefan Schiller, Mainz (DE); Simon Geissler, Bad Homburg (DE)

(73) Assignee: MERCK PATENT GMBH, Darmstadt (DE)

( * ) Notice: Subject to any disclaimer, the term of this patent is extended or adjusted under 35 U.S.C. 154(b) by 844 days.

(21) Appl. No.: 17/438,247

(22) PCT Filed: Mar. 10, 2020

(86) PCT No.: PCT/EP2020/056339

§ 371 (c)(1),
(2) Date: Sep. 10, 2021

(87) PCT Pub. No.: WO2020/182807

PCT Pub. Date: Sep. 17, 2020

(65) Prior Publication Data

US 2022/0184223 A1 Jun. 16, 2022

(30) Foreign Application Priority Data

Mar. 13, 2019 (EP) .................................... 19162511

(51) Int. Cl.
*G01N 33/543* (2006.01)
*A61K 47/65* (2017.01)
*A61K 47/68* (2017.01)

(52) U.S. Cl.
CPC ......... *G01N 33/5432* (2013.01); *A61K 47/65* (2017.08); *A61K 47/6891* (2017.08)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,571,894 A | 11/1996 | Wels et al. | |
| 5,587,458 A | 12/1996 | King et al. | |
| 7,198,945 B2 | 4/2007 | Nagamune et al. | |
| 8,940,501 B2 | 1/2015 | Ploegh et al. | |
| 10,260,038 B2 * | 4/2019 | Swee | A61P 31/12 |
| 2011/0321183 A1 | 12/2011 | Ploegh et al. | |

FOREIGN PATENT DOCUMENTS

| | | |
|---|---|---|
| CN | 101778937 A | 7/2010 |
| CN | 102037004 A | 4/2011 |
| EP | 1283257 A2 | 2/2003 |
| EP | 2825156 B1 | 7/2017 |
| WO | 93/16185 A2 | 8/1993 |
| WO | 10087994 A2 | 8/2010 |

OTHER PUBLICATIONS

John R. Silvius ei al: "A Novel 1-19 "Prebinding" Strategy Dramatically Enhances Sortase-Mediated Coupling of Proteins to Liposomes", Bioconjugate Chemistry, vol. 28, No. 4, Apr. 6, 2017.

Woll Steffen ei al: Sortagged anti-EGFR 1-19 iniiiunoliposomes exhibit increased cytotoxicity on target cells, European Journal of Pharmaceutics and Biopharmaceutics, vol. 136, Jan. 21, 2019 (Jan. 21, 2019), pp. 203-212, XP085600103, ISSN: 0939-6411.

Woll Steffen et al: "Sortaggable 1-19 liposomes: Evaluation of reaction conditions for single-domain antibody conjugation by Sortase-A and targeting of CD11b+myeloid cells", European Journal of Pharmaceutics and Biopharmaceutics, Elsevier Science Publishers B.V., Amsterdam, NL, vol. 133, Sep. 25, 2018 (Sep. 25, 2018), pp. 138-150.

Woll Steffen et al: "Pentaglycine lipid 1-19 derivates—rp-HPLC analytics for bioorthogonal anchor molecules in targeted, multiple-composite liposomal drug delivery systems", International Journal of Pharmaceutics, vol. 547, No. 1-2, Aug. 1, 2018 (Aug. 1, 2018), pp. 602-610.

Travis J. Antes et al: "Targeting 20 extracellular vesicles to injured tissue using membrane cloaking and surface display", Journal of Nanobiotechnology, vol. 16, No. 1, Aug. 30, 2018 (Aug. 30, 2018).

Christopher Bachran et al: "The activity 1-20 of niyeloid cell-specific VHH imunotoxins is target-, epitope-, subset- and organ dependent", Scientific Reports, vol. 7, No. 1, Dec. 1, 2017 (Dec. 1, 2017).

Urara Tomita : Studies on Enzymatic Protein Cell-Surface Anchoring Method and Application to Dendritic Cell Immunotherapy [online], A Dissertation Submitted to the Graduate School of Life and Environmental Sciences, the University of Tsukuba 2018, Internet: URL:https://tsukuba.repo.nii.ac.jp/records/46920 (pp. 1-72).

Won, et al., "Cell surface engineering to enhance mesenchymal stem cell migration toward an SDF-1 gradient", Biomaterials, vol. 35, No. 21, Jul. 2014, pp. 5627-5635.

Yamamoto, et al., "Interaction of poly(ethylene glycol)-conjugated phospholipids with supported lipid membranes and their influence on protein adsorption", Science and Technology of advanced MaTerialS, vol. 17, No. 1, Oct. 2016, pp. 677-684.

Zhang, et al., "Excessive activated T-cell proliferation after anti-CD19 CAR T-cell therapy", Gene Therapy, vol. 25, 3, Jun. 2018, pp. 198-204.

Antos, et al., "Lipid modification of proteins through sortase-catalyzed transpeptidation", Journal of the American Chemical Society, vol. 130, No. 48, Nov. 6, 2008, pp. 16338-16343.

Balint, et al., "The Pharmacology of Monoclonal Antibodies", Springer-Verlag, New York, vol. 113, 1994, pp. 269-315.

(Continued)

*Primary Examiner* — Blaine Lankford
(74) *Attorney, Agent, or Firm* — EMD SERONO RESEARCH INSTITUTE

(57) ABSTRACT

The present invention relates to a process for the preparation of a conjugate, comprising a biological molecule, an enzymatic tag, a hydrophilic spacer, a linker and a lipophilic moiety using enzymatic coupling.

19 Claims, 12 Drawing Sheets

Specification includes a Sequence Listing.

(56) References Cited

OTHER PUBLICATIONS

Bourel-Bonnet, et al., "A novel family of amphilic α-oxo aldehydes for the site-specific modification of peptides by two palmitoyl groups in solution or in liposome suspensions", Tetrahedron Letters, vol. 42, No. 39, Sep. 24, 2001, pp. 6851-6853.
Braisted, et al., "Synthesis of proteins by subtiligase", Methods in enzymology, vol. 289, 1997, pp. 298-313.
Braun, et al., "Bioorthogonal strategies for site-directed decoration of biomaterials with therapeutic proteins", Journal of Controlled Release, vol. 273, Mar. 10, 2018, pp. 68-85.
Clackson, et al., "Making Antibody Fragments using Phage Display Libraries", Nature, vol. 352, Aug. 15, 1991, pp. 624-628.
Desmyter, et al., "Antigen Specificity and High Affinity Binding Provided by One Single Loop of a Camel Single- domain Antibody", Journal of Biological Chemistry, vol. 276, No. 28, Jul. 13, 2001, p. 26285-26290.
Dixon, et al., "Nomenclature and symbolism for amino acids and peptides", Pure and Applied Chemistry, vol. 56, No. 5, 1984, pp. 595-624.
Epand, Richardm. , "Biophysical studies of lipopeptide-membrane interactions", Peptide Science, vol. 43, No. 1, 1997, pp. 15-24.
Ewert, et al., "Biophysical Properties of Camelid VHH Domains Compared to Those of Human VH3 Domains", Biochemistry, vol. 41, No. 11, Feb. 19, 2002, pp. 3628-3636.
Glasgow, et al., "In Vivo Site-Specific Protein Tagging with Diverse Amines Using an Engineered Sortase Variant", Journal of the American Chemical Society, vol. 138, No. 24, Jun. 2016, pp. 7496-7499.
Guo, et al., "New method for site-specific modification of liposomes with proteins using sortase A-mediated transpeptidation", Bioconjugate chemistry, vol. 23, No. 3, Mar. 21, 2012, pp. 650-655.
Hacein-Bey-Abina, et al., "LMO2-associated clonal T cell proliferation in two patients after gene therapy for SCID-X1", science, vol. 302, No. 5644, Nov. 2003, pp. 415-419.
Huston, et al., "Protein engineering of antibody binding sites: recovery of specific activity in an anti-digoxin single- chain Fv analogue produced in Escherichia coli.", Proceedings of the National Academy of Sciences, vol. 85, No. 16, Aug. 15, 1988, pp. 5879-5883.
Iden, et al., "In vitro and in vivo comparison of immunoliposomes made by conventional coupling techniques with those made by a new post-insertion approach", Biochimica et Biophysica Acta (BBA)-Biomembranes, vol. 1513, No. 2, Sep. 2001, pp. 207-216.
Ishida, et al., "A combinatorial approach to producing sterically stabilized (Stealth) immunoliposomal drugs", FEBS letters, vol. 460, No. 1, Oct. 22, 1999, pp. 129-133.
Kirpotin, et al., "Sterically Stabilized Anti-HER2 Immunoliposomes: Design and Targeting to Human Breast Cancer Cells in Vitro", Biochemistry, vol. 36, No. 1, Jan. 7, 1997, pp. 66-75.
Kohler, et al., "Continuous Cultures of Fused Cells Secreting Antibody of Predefined Specificity", Nature, vol. 256, Aug. 7, 1975, pp. 495-497.
Lee, et al., "Cell surface engineering and application in cell delivery to heart diseases", Journal of Biological Engineering, vol. 12, No. 1, Dec. 4, 2018, pp. 1-11.
Lee, et al., "One-Step Method for Instant Generation of Advanced Allogeneic NK Cells", Advanced Science, vol. 5, No. 11, Nov. 2018, pp. 1-11.
Liebscher, et al., "N-terminal protein modification by substrate-activated reverse proteolysis", Angewandte Chemie International Edition, vol. 53, 11, Mar. 10, 2014, pp. 3024-3028.
Lim, et al., "Cell surface-engineering to embed targeting ligands or tracking agents on the cell membrane", Biochemical and biophysical research communications, vol. 482, No. 4, Jan. 22, 2017, pp. 1042-1047.
Lith, et al., "Legomedicine-A Versatile Chemo-Enzymatic Approach for the Preparation of Targeted Dual-Labeled Llama Antibody-Nanoparticle Conjugates", Bioconjugate Chemistry, vol. 28, No. 2, Jan. 3, 2017, pp. 539-548.
Marks, et al., "By-passing immunization: human antibodies from V-gene libraries displayed on phage.", Journal of molecular biology, vol. 222, No. 3, Dec. 5, 1991, pp. 581-597.
Marqués-Gallego, et al., "Ligation strategies for targeting liposomal nanocarriers", BioMed research international, vol. 2014, No. 1, Jul. 2014, pp. 1-12.
Martin, et al., "Non-Natural Cell Surface Receptors: Synthetic Peptides Capped with N-Cholesterylglycine Efficiently Deliver Proteins into Mammalian Cells", Bioconjugate chemistry, vol. 14, No. 1, Nov. 15, 2002, pp. 67-74.
Miura, et al., "Encapsulation of islets with ultra-thin polyion complex membrane through poly(ethylene glycol)-phospholipids anchored to cell membrane", Biomaterials, vol. 27, No. 34, Dec. 2006, pp. 5828-5835.
Nguyen, et al., "Butelase 1 is an Asx-specific ligase enabling peptide macrocyclization and synthesis", Nature chemical biology, vol. 10, No. 9, Jul. 20, 2014, pp. 732-738.
Noble, et al., "Ligand-targeted liposome design: challenges and fundamental considerations", Trends in biotechnology, vol. 32, No. 1, Jan. 2014, pp. 32-45.
Nuijens, et al., "Chemo-enzymatic peptide synthesis (CEPS) using omniligases and selective peptiligases Efficient biocatalysts for assembling linear and cyclic peptides and protein conjugates", Chimica Oggi-Chemistry Today, vol. 34, No. 6A, Nov. 2016, pp. 16-19.
Nuijens, et al., "Engineering a Diverse Ligase Toolbox for Peptide Segment Condensation", Advanced Synthesis & Catalysis, vol. 358, No. 24, Dec. 22, 2016, pp. 4041-4048.
Oswald, et al., "Determination of the activity of maleimide-functionalized phospholipids during preparation of liposomes", International Journal of Pharmaceutics, vol. 514, No. 1, Nov. 30, 2016, pp. 93-102.
Paulick, et al., "Synthetic Analogues of Glycosylphosphatidylinositol-Anchored Proteins and Their Behavior in Supported Lipid Bilayers", Journal of the American Chemical Society, vol. 129, No. 37, Aug. 23, 2007, p. 11543-11550.
"International Preliminary Report on Patentability received for PCT Application No. PCT/EP2020/056339, mailing date Sep. 23, 2021", 09 Pages.
"International Search Report and Written Opinion received for PCT Application No. PCT/EP2020/056339, mailing date May 26, 2020", 15 Pages.
Pishesha, et al., "Engineered erythrocytes covalently linked to antigenic peptides can protect against autoimmune disease", Proceedings of the National Academy of Sciences, vol. 114, No. 12, Mar. 7, 2017, pp. 3157-3162.
Pulsipher, et al., "Directing Neuronal Signaling through Cell-Surface Glycan Engineering", Journal of the American Chemical Society, vol. 136, No. 19, Apr. 18, 2014, pp. 6794-6797.
Ritzefeld, Dr. Markus, "Sortagging: a robust and efficient chemoenzymatic ligation strategy", Chemistry-A European Journal, vol. 20, No. 28, Jul. 7, 2014, pp. 8516-8529.
Ruella, et al., "Induction of resistance to chimeric antigen receptor T cell therapy by transduction of a single leukemic B cell", Nature medicine, vol. 24, No. 10, Oct. 2018, pp. 1499-1503.
Saxon, et al., "Cell surface engineering by a modified Staudinger reaction", Science, vol. 287, No. 5460, Apr. 2000, pp. 2007-2010.
Schmidt, et al., "Enzyme-mediated ligation technologies for peptides and proteins", Current opinion in chemical biology, vol. 38, Jun. 2017, pp. 1-7.
Skerra, et al., "Assembly of a functional immunoglobulin Fv fragment in *Escherichia* coli", Science, vol. 240, No. 4855, May 20, 1988, pp. 1038-1041.
Steffen, et al., "In vitro characterization of a bivalent anti-HER-2 affibody with potential for radionuclide-based diagnostics", Cancer biotherapy & radiopharmaceuticals, vol. 20, No. 3, Jun. 30, 2005, pp. 239-248.
Swee, et al., "One-Step Enzymatic Modification of the Cell Surface Redirects Cellular Cytotoxicity and Parasite Tropism", ACS chemical biology, vol. 10, No. 2, Oct. 31, 2014, pp. 460-465.
Tabata, et al., "Development of a Sortase A-mediated Peptide-labeled Liposome Applicable to Drug-delivery Systems", Anticancer Research, vol. 35, No. 8, Aug. 2015, pp. 4411-4417.

(56) References Cited

OTHER PUBLICATIONS

Tabata, et al., "Investigation on the reaction conditions of Staphylococcus aureus sortase A for creating surface- modified liposomes as a drug-delivery system tool", Anticancer Research, vol. 34, No. 8, Aug. 2014, pp. 4521-4527.
Takemoto, et al., "Islet Surface Modification with Urokinase through DNA Hybridization", Bioconjugate chemistry, vol. 22, No. 4, Mar. 9, 2011, pp. 673-678.
Tang, et al., "Enhancing T cell therapy through TCR-signaling-responsive nanoparticle drug delivery", Nature biotechnology, vol. 36, No. 8, Jul. 9, 2018, pp. 707-716.
Tomita, et al., "Protein cell-surface display through in situ enzymatic modification of proteins with a poly(Ethylene glycol)-lipid", Biotechnology and Bioengineering, vol. 110, No. 10, Oct. 2013, pp. 2785-2789.
Ton-That, et al., "Purification and characterization of sortase, the transpeptidase that cleaves surface proteins of Staphylococcus aureus at the LPXTG motif", Proceedings of the National Academy of Sciences, vol. 96, No. 22, Oct. 26, 1999, p. 12424-12429.

* cited by examiner (1) (2) (3)

PROCESS FOR THE PREPARATION OF LIPIDATED PROTEINACEOUS STRUCTURES

The present invention is related to a process for the preparation of peptide and protein-lipid conjugates exhibiting strong interaction with hydrophobic surfaces and membranes while being soluble in a neat aqueous dispersion. The conjugates obtained by such process are usable for surface engineering of hydrophobic polymeric surfaces, drug delivery systems and cells.

The invention relates to a process for the preparation of a conjugate, comprising a biological molecule, an enzymatic tag, a hydrophilic spacer, a linker and a lipophilic moiety using enzymatic coupling. The lipophilic moiety conjugated to the biological molecule is utilized to anchor the biological molecule on either hydrophobic polymeric surface, the surface of lipid-based drug delivery systems (DDS, such as liposomes) or whole living cells [1].

The anchorage of biological molecules on drug delivery systems has the purpose to achieve a targeted drug delivery to cells, which means that carrier-encapsulated drugs are directed towards desired cell types via a ligand-target interaction. Using this interaction, pharmacokinetics as well as pharmacodynamic properties of the drug may be improved. This may especially include the delivery of toxic compounds towards cancer cells.

The anchorage of biological molecules on cells is especially relevant for therapies which include adoptive cell transfers. Here, cells such as stem cells or immune cells derived from the patient or from another individual are cultured and modified ex vivo and are then returned to the patient. Typical therapeutic applications include cancer immunotherapy, autoimmune diseases, regenerative medicine, and tissue engineering. These therapeutic areas may profit if the surface of the cells involved is modified in a supraphysiological fashion, e.g. during immune therapies by anchorage of cytokines [2], during regenerative therapies by anchorage of ligands leading to an increased chemotaxis of mesenchymal stem cells [3, 4] or during treatment of autoimmune diseases by anchorage of antigens and enzymes on cells [5, 6].

Genetic engineering can be used for cell membrane engineering, thereby offering genetic inheritability for subsequent daughter cells or the possibility to simultaneously achieve extra- and intracellular modifications. However, genetic engineering suffers from several drawbacks. These include the use of viral vectors, which may be responsible for immunogenic reactions, overactivation (due to constitutive expression [7]) or de novo tumorigenesis [8, 9]. Genetic engineering strongly depends on the transduction or transfection efficiency, which is hard to predict. Hence, the therapeutic efficacy of the modified cells may show inconsistent therapeutic efficacy. Also, modifications are not possible with all cell types, e.g. slowly dividing cells [1]. Finally, genetic engineering leads to permanent and irreversible inherent modifications, what may not be desired in every therapeutic case [1].

Non-genetic methods are important alternatives to genetic engineering of cellular surfaces and can be divided into modifications based on covalent conjugation of structures to the cell membrane or hydrophobic insertion. Covalent conjugation makes use of reactive structures present on the cellular surface to attach the desired structures [1]. A major drawback of these chemical methods are the resulting heterogeneous conjugation products, since a plethora of possible reaction sites such as carboxylic acids, cysteines, lysines or carbohydrate structures are involved in linkage of the bioactive binder and the cell surface. Therefore, also site-specific click chemistry [10, 11] was employed to conjugate proteins to cellular surfaces. These site-specific chemical reactions require either (genetic) introduction of suitable accessor molecules on the cellular surface, or may require potentially toxic catalysts or may still lead to several by-products [10].

Hydrophobic insertion is an option to circumvent a direct modification of existing structures on the cellular surface [1]. It involves lipidation of the bioactive binder as isolated reaction, and a subsequent affinity-based spontaneous insertion of the lipidated structure into the bilayer of membranes. Since liposomal drug delivery systems are also build on a bilayer structure, their membranes can be modified with lipidated biological molecules as well. This process is commonly referred to as "post-insertion" [12].

Anchorage of compounds into the cell membrane via hydrophobic insertion is described to be non-toxic. Also, the inserted molecules can participate in the dynamic movement of the cell membrane [1]. Compared to a covalent attachment, hydrophobic insertion avoids dependency of the degree of cell modification from the reaction efficacy. Also, physiological alterations like reduction of cell membrane mobility or alterations of functional structures present on the cell surfaces are mitigated [1]. Hydrophobic insertion was used in several reports to achieve a cell membrane modification with polyethylene glycols [13, 14], glycans [15], oligonucleotides [6] and peptides or proteins [4, 16-19]. The above listed reports on protein lipidation and cell insertion indicate promising processes and results for cell membrane engineering. However, several major disadvantages hamper a proper use e.g. for cell membrane remodeling during cell therapies in humans. Martin et al. reported the lipidation of peptides with a sterol-like lipid anchor [17]. This step was conducted on a solid phase and required harsh reaction conditions, including extensive use of protective groups for carboxylic acids since the reaction was based on a PyBOP (benzotriazol-1-yl-oxytripyrrolidinophosphonium hexafluorophosphate)/HOBT (Hydroxybenzotriazole) activating step. Also, organic solvents like dimethylformamide were required. This procedure is therefore rather not applicable for large proteins which possess several reactive sites, and where a selective protection of the amino acid side chains is not be possible. Furthermore, a huge variety of side products could be expected from using such a lipidation procedure for large proteins.

In order to improve the treatment of myocardial infarctions in a regenerative manner, Won et al. conjugated a recombinant CXC chemokine receptor 4 (CXCR4) to PEGylated lipids with two hydrophobic, saturated myristyl chains and modified the surface of mesenchymal stem cells (MSC) by hydrophobic insertion [4]. This improved the migration of the so modified MSCs in an in vitro assay, thus potentially increasing the homing of MSCs to ischemic sites in the myocardium [1]. Since CXCR4 possesses eight cysteines which are accessible for reaction with the utilized maleimide modified lipid, manifold structural isomers of lipidated CXCR4 or multiple-conjugated species can be expected after lipid modification [4]. These may have different biological activities or may lead to different interaction of the inserted structure with the cellular bilayer. This may subsequently lead to different steric accessibilities of the binding regions of the receptor, and finally to potentially reduced binding of the respective ligands. In another study, the same group conjugated di-myristylated, PEGylated lipids to an antibody-drug conjugate similar to the marketed product Kadcyla® [20]. The lipid consisted of a dimyristyl-motif as hydrophobic anchor and a polyethylene glycol spacer of non-described length, whose terminal carboxylic acid group was activated via carbodiimide-NHS chemistry. This structure preferentially couples towards the primary amines of the side chain of lysines in proteins, of which up to 70 from 88 are described to be reactive in the antibody of Kadcyla® [10]. The unavoidable heterogeneity leads to multiple concerns from therapeutic, safety and also regulatory/analytical perspectives.

Such heterogeneity might be mitigated with a suitable site-selective conjugation strategy. Sortase mediated transpeptidation for lipidation of biological molecules is a promising approach covering above mentioned problems, since the reaction has a marked versatility, the conjugation is feasible at mild reaction conditions, and has an inherent site specificity due to conjugation between defined amino acid tags. The enzyme family of sortases belong to the transpeptidases, originally discovered as house-keeping enzymes in gram-positive bacteria, where they mediate protein anchoring on the peptidoglycan layer [21]. Sortase A variant, derived from *Staphylococcus aureus*, recognizes a C-terminal LPxTG-motif (leucine—proline—any amino acid—threonine—glycine) in the target protein and forms a thioacyl intermediate with the threonine and a cysteine in the catalytic center of the enzyme [21].

Equation 1: General scheme of sortase A mediated transpeptidation $$\text{Protein-LPxTG}-R_1-\text{COOH} + H_2N-G-R_2 \xrightarrow{\text{Sortase-A}} \text{Protein-LPxTG}-R_2 + H_2N-G-R_1-\text{COOH}$$

The amide bond towards the glycine is cleaved and subsequently replaced via the transpeptidation reaction with an incoming nucleophilic N-terminus e.g. of oligoglycines [21] or other primary amines [22, 23].

An attempt to implement such a sortase A based conjugation strategy to hydrophobic insertion based cell membrane engineering was done by Antos et al. [16]. Antos et al. used the transpeptidase sortase A to attach triglycine-modified alkyl chains ranging from 10 to 22 carbons as well as triglycine-modified cholesterol and an adamantan derivate to an LPETG-modified eGFP (enhanced green fluorescent protein, a model protein). They showed efficient association of the lipidated eGFP with cells for alkyl chain lengths equal or longer than 14 carbon atoms, as well as for cholesterol used as lipid anchor. However no association of adamantan-lipidated eGFP was found with cellular bilayers. Despite these promising results, the study demonstrated by Antos et al. has several disadvantages. First, only single lipid chains were attached to the protein, although previous reports stated the requirement of two lipid chains for a reliable and stable anchorage of proteinaceous structures in the membrane [24, 25]. Most likely, Antos et al. circumvented solubility issues—which are a major challenge during protein lipidation—by usage of single-lipid chain modifications. These solubility issues for long chained anchors were further mitigated by the use of the detergence n-dodecyl maltoside during the lipidation of eGFP with an C22 alkyl chain—the most promising anchor for cell interaction. Usage of detergents during lipidation of proteins is unfavorable, since both detergents and lipid structure have similar polarity, what may hamper a proper purification e.g. by chromatography. Similarly, depletion of detergents from the lipidated product may lead to stability issues due to the hydrophobicity of the obtained product. Finally, detergents may be toxic, hampering a usage of the lipidated product on cells, e.g. during autologous therapies in humans, or detergents may impact integrity of the lipidated protein through denaturation. Since the eGFP lipidated either with cholesterol or the C22 alkyl chain anchor showed pronounced internalization in different cell lines after 5 h, it is also questionable whether these lipid anchors serve as suitable tool to stably remodel the exterior side of cell membranes. Also, since no spacer between lipid anchor and protein was utilized, it may be questionable whether potential binders immobilized on the cellular surface can be accessible for their target structures [26]. Another drawback of the process demonstrated by Antos et al. is the affinity based purification method. Since both eGFP and sortase A carry a $His_6$-tag, and this Hiss-tag is cleaved from the eGFP during reaction with the lipid, a Ni-NTA resin containing 1 M NaCl and 40 mM imidazole was used to bind and subsequently remove all Hiss-tagged proteins. This strategy neglects that also other compounds present in the reaction bulk have to be removed, in particular the non-conjugated lipid. Therefore, the process presented by Antos et al. is in the disclosed form not suitable for a usage of the lipidated product during e.g. in vivo studies or cell therapies.

Nagamune et al. combined a hydrophobic insertion of triglycine lipids (which comprised a polyethylene glycole spacer between hydrophobic moiety and triglycine unit) into cells with a subsequent sortase A mediated conjugation of LPETG modified proteins [19, 27]. This process can therefore be regarded as a combination of hydrophobic insertion and covalent conjugation strategy for cell membrane engineering. The authors reported that eGFP could be successfully conjugated to the triglycine-modified membrane of a cancer cell line. Additionally, the conjugation of the Fc fragment of an immunoglobulin led to an increased phagocytosis of the cancer cells via co-incubation with dendritic cells. Although the combined strategy of hydrophobic insertion and covalent conjugation is a gentle approach, several important disadvantages hamper a proper use of it, e.g. during in vivo treatments. First, sortase A is known to conjugate LPETG-modified proteins unselectively to N-terminal glycines present at the surface of cellular membranes [28] or in the cell-surrounding matrix/fluid. Therefore, the major advantage of sortase A—the generation of highly defined reaction products—is lost, since a variety of conjugates of either the model protein eGFP or the Fc fragment with cellular surface proteins can be assumed. Furthermore, no determination of residuals of sortase A after the cell washing was shown. Since sortase A is a protein that may adsorb to large surfaces like cellular membranes, an exhaustive depletion from a cell bulk may be a very challenging task. Exposure of cells to sortase A may lead to unspecific adsorption [29], and thus considerable residuals on the cellular surface even after purification. Those may lead to reverse reactions, meaning a cleavage of the conjugated structure from the cells, or more dramatically, serious immune reactions upon administration of cells.

Also drug delivery systems are modified with a process analogue to the hydrophobic insertion process for cell membrane engineering. This so called post-insertion process describes the insertion of lipidated ligands either from a neat micelles or from mixed micelles composed of lipidated ligand and PEGylated lipid [12, 30-32]. The derivatization of the proteinaceous structure, which is typically employed as a targeting ligand [33] on the drug delivery system, occurs mainly via unspecific chemical reactions [31]. Up to date, no site-selective strategy for a immunoliposome preparation with post-insertion was disclosed, although several site-selective conjugation strategies for "in situ" conjugation (or "post-derivatization) of ligands onto the liposomal surface have been revealed [31]. Although these techniques provide distinct improvement over the previously utilized non-selective conjugation methods, they still suffer from drawbacks like requirement of various catalysts, unknown toxicity of the used linkers and/or reaction products, or a significant amount of by-products [10]. Enzymatic techniques may improve this issue, and several reports describe the successful conjugation of model proteins [34-36] or targeting ligands [29, 37, 38] onto the liposomal surface. However, onsite conjugation with enzymes is challenging, since enzymes may be hard to remove from reaction bulk, thus potentially impacting safety due to immunogenicity and also stability (due to reverse reactions) of the drug delivery system [29].

The above described processes known in the art for the lipidation of proteinaceous structures with subsequent derivatization of drug delivery systems or cell membranes have several disadvantages and/or lead to either chemical or cellular products with insufficient properties regarding homogeneity or purity. It was the object of the present invention to provide a process for the production of suitable protein-lipid conjugates that overcome such disadvantages, meaning it should yield a site-selectively lipidated product which is free of residuals derived from the reaction process, a product which is soluble without the need of additives such as detergents, and it should provide non-altered biological function as well as activity when being present on complex surfaces such as cell membranes.

Therefore, one object of the present invention is directed to a process for the preparation of a conjugate, wherein the conjugate comprises a biological molecule, an enzymatic tag, a hydrophilic spacer, a linker and a lipophilic moiety, such process comprises enzymatic coupling of a component comprising the enzymatic tag, the hydrophilic spacer, the linker and the lipophilic moiety with the biological molecule in an aqueous medium and purification of the conjugate. Advantageously, such process can be run without the use of any detergent.

It is further object of the invention to insert these molecules into hydrophobic environments, such as hydrophobic polymeric surfaces, lipid based drug delivery systems or membranes of living cells.

As used herein, the term "component comprising the enzymatic tag, the hydrophilic spacer, the linker and the lipophilic moiety" is also referred to as "Component A"

According to a preferred embodiment, the enzymatic tag, the hydrophilic spacer, the linker and the lipophilic moiety constituting Component A to be coupled with the biological molecule are interlinked in order as they are mentioned (i.e. enzymatic tag—hydrophilic spacer—linker—lipophilic moiety).

As used herein, "a" or "an" shall mean one or more. As used herein when used in conjunction with the word "comprising," the words "a" or "an" mean one or more than one. As used herein "another" means at least a second or more. Furthermore, unless otherwise required by context, singular terms include pluralities and plural terms include the singular.

As used herein, the term "biological molecule" refers to a natural or synthetic molecule having, as a rule, a molecular weight greater than approximately 300, and is preferably a poly- or oligosaccharide, an oligo- or polypeptide, a protein, a peptide, a poly- or oligonucleotide as well as a glycosylated lipid derivative thereof. Most typically, the biological molecule is an immunotherapeutic agent, an antibody or a fragment thereof, a functional derivative of any of these antibodies or fragments including fusion proteins.

As used herein, the term "enzymatic tag" refers to a moiety that is recognizable by an enzyme and that identifies the molecule linked to such tag as a substrate for the reaction catalyzed by such enzyme. When reacted with the enzyme the enzymatic tag may be removed in part or in total. In the present invention the enzymatic tag is on the terminal end of the component comprising such enzymatic tag, the hydrophilic spacer, the linker and the lipophilic moiety and directly linked with the hydrophilic spacer. The enzymatic tag allows such component to be coupled to the biological molecule via enzymatic reaction. After coupling of the component with the biological molecule all or a part of the moiety of the enzymatic tag remains in the conjugate resulting from such coupling.

As used herein, the term "hydrophilic spacer" refers to a moiety present between specific elements of the conjugate or Component A that is hydrophilic and thereby provides some hydrophilicity to such conjugate or Component A. In the present invention the hydrophilic spacer is present between the enzymatic tag and the linker. The hydrophilic spacer used in the present invention is not subject to any limitation, as long as it increases the water solubility of the component or conjugate.

As used herein, the term "linker" refers to a chemical moiety comprising a covalent bond or a chain of atoms that covalently attaches a first molecule to a second molecule through chemical bonds. In the present invention a linker is used to link the hydrophilic spacer with the lipophilic moiety.

As used herein, the term "lipophilic moiety" refers to any hydrophobic group that is soluble in or miscible with fats, oils, lipids, and lipophilic non-polar solvents such as hexane or toluene.

As used herein, the term "purification" refers to a process step of reducing the amounts of foreign elements, such as side reaction products (e.g. fragments of the enzyme substrates that inevitably emerge during the conjugation, the enzyme itself or required co-factors for the reaction, or unreacted substrates) that are not the conjugate and that may be present in the medium after performing the enzymatic reaction. The purification may involve different methods known in the art such as chromatographic methods and may include one or more steps, such as chromatographic steps.

The biological molecule present in the conjugate is a polypeptide. Accordingly, the present invention is directed to a process, wherein the biological molecule is a polypeptide.

The term "polypeptide" as used herein refers to a polymer of amino acids, typically L-amino acids, connected one to the other, typically by peptide bonds between the α-amino and carboxyl groups of adjacent amino acids by amide linkages, wherein the number of amino acid residues can range from about 5 to about one million. Preferably, a polypeptide has from about 10 to about 2000 amino acid residues and, even more preferably from about 20 to about 500 amino residues. Thus, as used herein, a polypeptide includes what is often referred to in the art as an oligopeptide (5-10 amino acid residues), a polypeptide (11-100 amino acid residues) and a protein (above 100 amino acid residues).

Appropriate polypeptides that may be present as a biological molecule include antigens, cell adhesion proteins including integrins and cadherins, peptide hormones, especially growth factors, cytokines, especially interleukins, receptors related to any these molecules, enzymes and natural or artificial antibodies and fragments thereof. Thus, the invention is further directed to the process, wherein the biological molecule conjugated to the "component A" is an antigen, a cell adhesion protein such as an integrin or a cadherin, a peptide hormone, such as a growth factor, a cytokine such as an interleukin, a receptor related to any of these molecules, an enzyme, or a natural or artificial antibody or a fragment thereof.

As used herein, the term "antigen" refers to an entity or fragment thereof which can bind to an antibody. An antigen can induce an immune response in an organism, particularly an animal, more particularly a mammal including a human. The term "antigen" includes regions known as antigenic determinants or epitopes which refers to a portion of the antigen (which are contacted or which play a significant role in supporting a contact residue in the antigen responsible for antigenicity or antigenic determinants).

As used herein, the term "cell adhesion protein" refers to a large family of cell adhesion proteins that have a extracellular region within the structure as a cell recognition site and that are involved in in the mediation of cell-to-cell interactions. The term "cell adhesion protein" includes proteins from natural sources or from recombinant cell culture and biologically active equivalents of the native-sequence of the adhesion protein, including synthetically produced small-molecule entities and pharmaceutically acceptable derivatives and salts thereof.

As used herein, the term "integrin" refers to a cell adhesion proteins that allows cells both to bind to and to respond to the extracellular matrix and is involved in a variety of cellular functions such as wound healing, cell differentiation, homing of tumor cells and apoptosis. Functional integrins consist of two transmembrane glycoprotein subunits, called alpha and beta, that are non-covalently bound. The alpha subunits all share some homology to each other, as do the beta subunits. The receptors always contain one alpha chain and one beta chain. Examples include alpha6beta1, alpha3beta1, alpha7beta1, LFA-1 etc. As used herein, the term "integrin".

As used herein, the term "cadherin" refers to a cell adhesion protein which is a member of the cadherin superfamily of proteins. The cadherin superfamily includes, for example, the subfamily of classical cadherins, specific examples of which include E-cadherin, N-cadherin, and P-cadherin, and the subfamily of desmosomal proteins, specific examples of which include desmogleins 1, 2 and 3, and desmocollin 3. Natural sources of cadherins may be found in vertebrates, including humans, farm animals, sport animals, primates, rodents and pets, for example, chickens, pigs, sheep, horses, cows, rabbits, mice and rats.

As used herein, the term "peptide hormone" refers to proteins with endocrine functions, for example insulin, proinsulin, parathyroid hormone, relaxin, prorelaxin, insulin, glucagon, calcitonin; glycoprotein hormones such as follicle stimulating hormone (FSH), thyroid stimulating hormone (TSH), and luteinizing hormone (LH).

As used herein, the term growth factor refers to proteins or polypeptides that are capable of stimulating cell growth. They include, but are not limited to, epidermal growth factor (EGF), human growth hormone (HGF), nerve growth factors such as NGFβ, N-methionyl human growth hormone, bovine growth hormone, hepatic growth factor, platelet-growth factor; transforming growth factors (TGFs) such as TGFα and TGFβ; fibroblast growth factor ephrins (Eph), erythropoietin (EPO), glia-cell stimulating factor (GSF); colony-stimulating factors (CSF) including macrophage colony-stimulating factor (M-CSF), granulocyte macrophage colony-stimulating factor (GM-CSF), and granulocyte colony-stimulating factor (G-CSF); stem cell growth factor (SCGF) (also called Steel Factor); stromal cell-derived factor (SDF), effective fragments thereof, and combinations thereof; and vascular endothelial growth factor (VEGF). Other growth factors can include hepatocyte growth factor (HGF), Angiopoietin-1, Angiopoietin-2, b-FGF, and FLT-3 ligand, and effective fragment thereof.

As used herein the term "cytokine" refers to proteins released by one cell population which act on another cell as intercellular mediators. Examples of such cytokines are lymphokines and monokines. Included among the cytokines are interleukin; prolactin; placental lactogen; mouse gonadotropin-associated peptide; inhibin; activin; thrombopoietin (TPO); interferons such as IFNα, IFNβ, and IFNγ; and TNFα or TNFβ.

As used herein, the term "interleukin" refers to any of a variety of cytokines secreted by immune cells that regulate a range of immune system functions. One skilled in art will understand that the presence or level of one or more interleukins including, without limitation, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24.

The term "antibody" or "immunoglobulin" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity. The term generally includes heteroantibodies which are composed of two or more antibodies or fragments thereof of different binding specificity which are linked together.

Depending on the amino acid sequence of their constant regions, intact antibodies can be assigned to different "antibody (immunoglobulin) classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ and μ respectively. Preferred major class for antibodies used as biological molecule is IgG, in more detail IgG1 and IgG2.

Antibodies are usually glycoproteins having a molecular weight of about 150,000, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains. The "light chains" of antibodies from any vertebrate species can be assigned to one of two clearly distinct types, called kappa (κ) and lambda (λ), based on the amino acid sequences of their constant domains.

"Antibody fragments" comprise a portion of an intact antibody, preferably comprising the antigen-binding or variable region thereof. Examples of antibody fragments include Fab, Fab', F(ab')2, Fv and Fc fragments, diabodies, linear antibodies, single-chain antibody molecules; and multispecific antibodies formed from antibody fragment(s). An "intact" antibody is one which comprises an antigen-binding variable region as well as a light chain constant domain (CL) and heavy chain constant domains, CH1, CH2 and CH3. Preferably, the intact antibody has one or more effector functions.

As used herein, the term "artificial" refers to compositions and systems that are designed or prepared by man, and are not naturally occurring. For example, an artificial polypeptide (e.g., antibody or antibody fragment) is one comprising a non-natural sequence (e.g., a polypeptide without 100 percent identity with a naturally-occurring protein or a fragment thereof).

As used herein, the term "artificial antibody", consistent with the definition of "artificial" above, refers to an antibody having a distinct amino acid sequence or chemical makeup from those found in natural antibodies. An artificial antibody is not a subsequence of a naturally occurring protein, either the wild-type (i.e., most abundant) or mutant versions thereof. An "artificial antibody", as used herein, may be produced or synthesized by any suitable method (e.g., recombinant expression, chemical synthesis, enzymatic synthesis, purification from whole animal, etc.).

According to a preferred embodiment of the invention the antibody used as biological molecule is a monoclonal antibody or a fragment thereof, such as a single-chain variable fragment (scFv), a variable fragment (Fv), or a fragment antigen binding (Fab, Fab' or F(ab')2), a camelid or cartilaginous fish-derived heavy-chain only antibody or a fragment thereof, such as a VHH or a vNAR, or wherein the artificial polypeptide is DARPin, an adnectine, an anticalin, or an affibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. Methods for making monoclonal antibodies include the hybridoma method described by Kohler and Milstein (1975, Nature 256, 495) and in "Monoclonal Antibody Technology, The Production and Characterization of Rodent and Human Hybridomas" (1985, Burdon et al., Eds, Laboratory Techniques in Biochemistry and Molecular Biology, Volume 13, Elsevier Science Publishers, Amsterdam), or may be made by well-known recombinant DNA methods (see, e.g., U.S. Pat. No. 4,816,567). Monoclonal antibodies may also be isolated from phage antibody libraries using the techniques described in Clackson et al., Nature, 352:624-628 (1991) and Marks et al., J. Mol. Biol., 222:58, 1-597 (1991), for example.

Papain digestion of antibodies produces two identical antigen-binding fragments, called "Fab" fragments, each comprising a single antigen-binding site and a CL and a CH1 region, and a residual "Fc" fragment, whose name reflects its ability to crystallize readily.

The "Fc" region of the antibodies comprises, as a rule, a CH2, CH3 and the hinge region of an IgG1 or IgG2 antibody major class. The hinge region is a group of about 15 amino acid residues which combine the CH1 region with the CH2-CH3 region.

Pepsin treatment yields an "F(ab')2" fragment that has two antigen-binding sites and is still capable of cross-linking antigen. A further treatment with suitable reducing agents such as Tris(2-carboxyethyl)phosphin (TCEP), β-Mercaptoethylamine or Dithiothreitol delivers Fab' fragments. "Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions (CDRs) of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. The Fab fragment also contains the constant domain of the light chain and the first constant domain (CH1) of the heavy chain. "Fab' " fragments differ from Fab fragments by the addition of a few residues at the carboxy terminus of the heavy chain CH1 domain including one or more cysteines from the antibody hinge region. F(ab')2 antibody fragments originally were produced as pairs of Fab' fragments which have hinge cysteines between them.

"Single-chain Fv" or "scFv" antibody fragments comprise the VH, and VL domains of antibody, wherein these domains are present in a single polypeptide chain. Preferably, the scFv polypeptide further comprises a polypeptide linker between the VH and VL domains which enables the scFv to form the desired structure for antigen binding. Single-chain Fv antibodies are known, for example, from Plückthun (The Pharmacology of Monoclonal Antibodies, Vol. 113, Rosenburg and Moore eds., Springer-Verlag, New York, pp. 269-315 (1994)), WO93/16185; U.S. Pat. Nos. 5,571,894; 5,587,458; Huston et al. (1988, Proc. Natl. Acad. Sci. 85, 5879) or Skerra and Plueckthun (1988, Science 240, 1038).

The term "heavy chain-only antibody" or "HCAb" as used herein refers to a functional antibody, which comprises heavy chains, but lacks the light chains usually found in antibodies. Camelid animals (such as camels, llamas or alpacas) or cartilaginous fish (such as shark, ray or skate) are known to produce HCAbs. Camelid and cartilaginous fish antibodies comprise a heavy chain, but lack a light chain. HCAbs derived by camelid animals or cartilaginous fish are referred to as "camelid derived heavy-chain only antibody" and "cartilaginous fish-derived heavy-chain only antibody", respectively.

The term "VHH" as used herein refers to a variable region of a heavy chain of a camelid antibody. As such, a VHH region from such a camelid antibody represents the minimal structural element required to specifically bind to an antigen of interest in these species. Camelid VHH domains have been found to bind to antigen with high affinity (Desmyter et al. (2001), J. Biol. Chem. 276:26285-90) and possess high stability in solution (Ewert et al. (2002), Biochemistry 41:3628-36).

The term "vNAR" as used herein refers to a single variable new antigen receptor (NAR) domain antibody fragment. vNAR fragments are single-domain antibody fragments derived from heavy-chain antibodies, such as shark immunoglobulin new antigen receptor antibodies (IgNARs).

The term "designed ankyrin repeat protein" or "DARPin" refers to an artificial polypeptide having high specificity and high binding affinity to a target protein, which is prepared via genetic engineering. DARPins are originated from natural ankyrin protein, and have a structure where at least 2 or at least 3 ankyrin repeat motifs, for example, 3, 4 or 5 ankyrin repeat motifs are repeated. For example, the DARPins comprising 3, 4 or 5 ankyrin repeat motifs may have a molecular weight of about 10 kDa, about 14 kDa, and about 18 kDa, respectively. DARPin includes a core part which carries out structural function and a target binding part outside of the core which binds to a target. The core part includes conserved amino acid sequence and the target binding part includes different amino acid sequence depending on the target.

The term "adnectine" as used herein refers to a monobody, which is a an artificial antibody, which is constructed using a fibronectin type III domain (FN3).

The term "anticalin" as used herein relates to an artificial antibody derived from a lipocalin specifically binding GPD1 and inhibiting GPD1 activity. An anticalin has a barrel structure which is formed by eight antiparallel beta-strands pairwise connected by loops and an attached α-helix and which they share with naturally occurring lipocalins.

The term "affibody" as used herein refers to a recombined protein comprised of one polypeptide chain, comprising a domain responsible for selective interaction with an antigen, e.g. a specific tumour marker like HER2 (e.g. C. Steffen, M. Wikman, V. Tolmachev, G. P. Adams, F. Y. Nilsson, S. Ståhl, J. Carlsson: In vitro characterization of a bivalent anti-HER-2 affibody with potential for radionuclide-based diagnostics, CancerBiother. Radiopharm, 20 (2005), pp. 239-248), which can be bound with another polypeptide ensuring better properties for binding with the antigen, higher stability and additional functions, e.g. the possibility to controllably bind with another substance or a solid surface. Its mass usually falls within a range between several and over a dozen kilodaltons.

According to a preferred embodiment the biological molecule present in the component used in the process of the present invention is a single-domain antibody derived from the variable domain of camelid heavy-chain only antibodies (VHH).

Enzymatic coupling of the biological molecule with Component A can be accomplished by use of transpeptidases such as a sortase. A preferred transpeptidase used in the process of the invention is sortase A.

To enable coupling of the biological molecule with Component A the biological molecule carries a C-terminal motif as recognition signal for the transpeptidase. Thus, in an appropriate embodiment of the process of the invention the biological molecule prior to its coupling with the component comprising the enzymatic tag, the hydrophilic spacer, the linker, and the lipophilic component moiety (Component A) carries a C-terminal motif for enzymatic conjugation by transpeptidases, preferably sortase A.

According to a suitable embodiment the biological molecule carries as C-terminal motif an amino acid sequence consisting of "leucine—proline—X—threonine—glycine" (LPXTG). In such C-terminal motif "X" can be any proteinogenic amino acid except cysteine and tryptophan. Therefore, the invention is also directed to a process, wherein the biological molecule prior to its coupling to the component comprises a C-terminal motif that consists of the amino acid sequence "leucine—proline—X—threonine—glycine" (LPXTG), wherein "X" can be any proteinogenic amino acid.

The term "proteinogenic amino acid" as used herein refers to one of the 21 amino acids that are directly encoded for protein synthesis by the genetic code of eukaryotes except cysteine and tryptophan. Accordingly, the proteinogenic amino acid X that is present in the C-terminal motif is one of the amino acids glycine, alanine, valine, leucine, isoleucine, methionine, phenylalanine, proline, serine, threonine, tyrosine, asparagine, glutamine, aspartic acid, glutamic acid, lysine, arginine and histidine, whereby glutamic acid is preferred. Thus, the invention is further directed to the process, wherein the proteinogenic amino acid present in the LPXTG motif is glycine, alanine, valine, leucine, isoleucine, methionine, phenylalanine, proline, serine, threonine, tyrosine, asparagine, glutamine, aspartic acid, glutamic acid, lysine, arginine or histidine, preferably glutamic acid.

The enzymatic tag comprises an N-terminal amino function. According to an appropriate embodiment such N-terminal amino function is provided by an aliphatic amine, a single glycine or a polypeptide sequence comprising one or more N-terminal glycine, preferably pentaglycine, which is C-terminally linked to the hydrophilic spacer. Therefore, the invention is also directed to a process, wherein the enzymatic tag is an aliphatic amine, a single glycine or a polypeptide sequence comprising one or more N-terminal glycine, preferably pentaglycine, which is C-terminally linked to the hydrophilic spacer.

The "N-terminal" in conjunction with an amino acid, or a polypeptide chain, refers to the free amine group on the amino acid, or the free amine group on the first amino acid residue of the polypeptide chain. Likewise, the "C-terminal" in conjunction with an amino acid, or a polypeptide chain, refers to the free carboxy group on the amino acid, or the free carboxy group on the final amino acid residue of the polypeptide chain.

As explained above the hydrophilic spacer increases the water solubility of the component or conjugate. Suitable hydrophilic spacers that can be present in Component A used in the process of the present invention include hydrophilic polymerized radicals (with an increased affinity for aqueous solutions), i.e. polymers containing repeating structural units that comprise one or more of hydrophilic (or polar) groups in their alkylene backbone. Examples of usable hydrophilic polymeric radicals include polyoxy($C_2$-$C_3$)alkylenes (e.g. polyethylene glycol (PEG) or polypropylene glycol (PPG)), polysaccharides (e.g. dextran, pullulan, chitosan, hyaluronic acid) and polyethyleneimines, whereby polyethylene glycol is preferred. Therefore, an appropriate embodiment of the present invention is further directed to the process wherein the component comprising the enzymatic tag, the hydrophilic spacer, the linker and the lipophilic moiety with the biological molecule used in such process is a polyoxy($C_2$-$C_3$)alkylene (e.g. polyethylene glycol or polypropylene glycol), a polysaccharide (e.g. dextran, pullulan, chitosan, hyaluronic acid), a polysialic acid, a polyethyleneimine, preferably polyethylene glycol.

A preferred hydrophilic spacer is "PEG" or "polyethylene glycol", which encompasses any water-soluble poly(ethylene oxide). Typically, "PEG" means a polymer that contains a majority, e.g. >50%, of subunits that are —$CH_2CH_2O$—. Different forms of PEG may differ in molecular weights, structures or geometries (e.g., branched, linear, forked PEGs, multifunctional, and the like). PEGs that may be present in Component A used in the process of the invention may be "—$OCH_2CH_2O(CH_2CH_2)_m$—" but also comprises forms wherein one terminal "—O—" group is substituted by a "—NH—" group leading to the formula "—$NHCH_2CH_2O(CH_2CH_2O)_m$—. In such m is 10 to 300, preferably 15 to 100, more preferably 20 to 70, even more preferably 25 to 50, especially preferably from 30 to 40 and most preferably 35.

The linker connects the hydrophilic spacer with the lipophilic moiety by covalent bond such as C—C, C—O, C—N, and C—S. Linker usable for coupling with the hydrophilic spacer and the lipophilic moiety as well as the coupling of the linker with a hydrophilic spacer and a lipophilic moiety is known in the art and described, for example, in EP 2825156 B1. In principle, a bifunctional agent (i.e., an agent with two functional (end)groups), preferably a heterobifunctional agent (i.e., an agent with two different functional (end)groups) is reacted and thereby coupled with the component comprising the hydrophilic spacer and the lipophilic moiety. Typical functional groups include, but are not limited to, groups such as succinimidyl esters, maleimides, and pyridyldisulfides. In some embodiments, the bifunctional agent is selected from, but not limited to, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol]ester (NH SPEO12), N-succinimidyl (4-iodoacetyl) aminobenzoate (SIAB), N-succinimidyl S-acetylthioacetate (SATA), m-maleimidobenzoyl-N-hydroxysuccinimide ester (MBS) and N-h-maleimidobutyryloxy-succinimide ester (GMBS), succinmidyl dicarbonyl pentane or disuccinimidyl suberate.

The component comprising the enzymatic tag, the hydrophilic spacer, the linker and the lipophilic moiety used in the process of the present invention may be prepared with any of such linkers. According to a preferred embodiment the linker used for the preparation of such component is isoglutamine, on the σ-position amide linked with a 3-amino-1,2-propanediol, and on the α-standing amine-function linked to the hydrophilic spacer. Within the component comprising the enzymatic tag, the hydrophilic spacer, the linker and the lipophilic moiety, the linker moiety has the following formula (I):

(I)

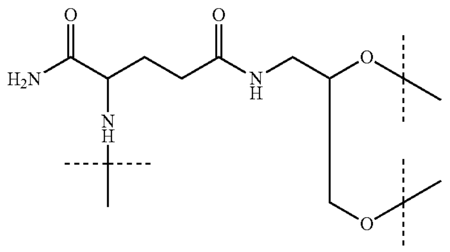

In such formula the dotted vertical line denotes an atomic bonding to the lipophilic moiety and the dotted vertical line denotes an bonding to the hydrophilic spacer.

According to an appropriate embodiment of the invention Component A used in the process contains as lipophilic moiety one or more, independently of each other, saturated or unsaturated, straight or branched hydrocarbon chains, such as fatty alcohols or fatty acids with chain lengths of 6-30 carbon atoms, or sterols such as cholesterol. Thus, the invention is also directed to a process wherein the lipophilic moiety present in Component A is or are one or more, independently of each other, saturated or unsaturated, straight or branched hydrocarbon chains, such as fatty alcohols or fatty acids with chain lengths of 6-30 carbon atoms, or sterols such as cholesterol. Preferably, the lipophilic moiety is a saturated straight hydrocarbon chain.

The term "fatty alcohol" as used herein refers to a long-chain aliphatic alcohol comprising from 6 to 30 carbon atoms and comprising at least one hydroxyl group OH. Preferably, the fatty alcohols have the structure R—OH with R denoting a linear alkyl group, optionally substituted with one or more hydroxyl groups, comprising from 6 to 30, better still from 10 to 30, or even from 10 to 22 and even better still from 14 to 18 carbon atoms. The fatty alcohols that can be used may be chosen, alone as a mixture, from lauryl alcohol (1-dodecanol), myristyl alcohol (1-tetradecanol), cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol) and myricyl alcohol (1-triacontanol). In Compound A the fatty alcohol and the linker are preferably connected with each other by an ether linkage $R^1$—O—$R^2$, whereby $R^1$ is the linker and $R^2$ is the alkyl group of the fatty alcohol.

The term "fatty acid" as used herein refers to long-chain aliphatic acids comprising at least 6 carbon atoms and comprising one or two, preferably one carboxylic acid groups. Preferably, the fatty acid has the structure R—COOH with R denoting a linear alkyl group comprising from 6 to 30, better still from 10 to 30, or even from 10 to 22 and even better still from 14 to 18 carbon atoms. Suitable fatty acids include, for example, n-decanoate (C10, caprate), n-dodecanoate (C12, laurate), n-tetradecanoate (C14, myristate), n-octadecanoate (C18, stearate), n-eicosanoate (C20, arachidate), n-docosanoate (C22, behenate), cis-6 9-octadecanoate (C18, oleate), all cis-6 5,8,11,14-eicosatetraenoate (C20, arachidonate) and the like. In Compound A the fatty acid is preferably connected with a linker having a hydroxyl group, whereby the carboxylic group of the fatty acid is preferably linked to the hydroxyl group of the linker via an ester linkage.

The term "sterol" as used herein refers to a steroid containing at least one hydroxyl group. A steroid is characterized by the presence of a fused, tetracyclic gonane ring system. Sterols include, but are not limited to, cholesterol (i.e., 2,15-dimethyl-14-(1,5-dimethylhexyl)tetracyclo [8.7.0.02,7.011,15]heptacos-7-en-5-ol). In Compound A the sterol and the linker are preferably connected with each other by an ether linkage $R^1$—O—$R^{2'}$, whereby $R^1$ is the linker and $R^{2'}$ is the ring system of the sterol.

According to an especially preferred embodiment of the invention Component A used in the process comprises two myristyl alcohols each ether linked to the diol-group of the 3-amino-1,2-propanediol of the linker. Thus, the invention is also directed to the process, wherein the lipophilic component moiety comprises two myristyl alcohols each ether linked to the diol-group of the 3-amino-1,2-propanediol.

According to an appropriate embodiment of the invention the process comprises the following steps (a) preparing an aqueous dispersion of a component comprising an enzymatic tag, a hydrophilic spacer, a linker and a lipophilic moiety; (b) adding an enzyme and a biological molecule; (c) incubating the mixture obtained in step (b) to produce the conjugate; (d) purifying the conjugate obtained in step (c). Therefore, the present invention is also directed to a process, which comprises the following steps (a) preparing an aqueous dispersion of a component comprising an enzymatic tag, a hydrophilic spacer, a linker and a lipophilic moiety;
(b) adding an enzyme and a biological molecule;
(c) incubating the mixture obtained in step (b) to produce the conjugate;
(d) purifying the conjugate obtained in step (c).

According to an appropriate embodiment of the invention the process uses a ligase as enzyme. The term "ligase" as used herein refers to an enzyme that can catalyse the joining of two large molecules by forming a new chemical bond, usually with accompanying hydrolysis of a small pendant chemical group on one of the larger molecules or the enzyme catalysing the linking together of two compounds, e.g., enzymes that catalyse joining of C—O, C—S, C—N, etc. In general, a ligase catalyses the following reaction: Ab+C→A–C+b. In the present invention the ligase is used to catalyse the hydrophilic spacer with the biological molecule.

Ligases usable in the present invention include sortase, butelase, trypsiligase, subtiligase, peptiligase and omniligase, whereby sortase A is preferred. Thus, the invention is further directed to a process, wherein the enzyme in step (b) is a ligase, including sortase, butelase, trypsiligase, subtiligase, peptiligase and omniligase, preferably sortase A.

Enzymes as used in the present invention are described, for example, by M Schmidt et al: Enzyme-mediated ligation technologies for peptides and proteins, Current Opinion in Chemical Biology (2017) 38, pp 1-7). More specifically, Sortase is described, for example, by T T Hung et al: Purification and characterization of sortase, the transpeptidase that cleaves surface proteins of *Staphylococcus aureus* at the LPXTG motif, PNAS, 1999, 96 (22) 12424-12429; Butelase by GKT Nguyen et al.: Butelase1 is an Asx-specific ligase enabling peptide macrocyclization and synthesis. Nat Chem Biol 2014, 10:732-738; Trypsiligase by S Liebscher et al.: N-Terminal Protein Modification by Substrate-Activated Reverse Proteolysis, Angewandte Chemie International Edition, 53-11, 1433-7851; Subtiligase by AC Braisted et al.: Synthesis of proteins by subtiligase. Methods Enzymol 1997, 289:298-313; Omniligase and Peptiligase by T Nuijens T et al.: Engineering of a diverse ligase toolbox for peptide segment condensation. Adv Synth Catal 2016, 358: 4041-4048 and by T Nuijens et al.: Omniligase and selective Peptiligases, efficient biocatalysts for assembling linear and cyclic peptides and protein conjugates, Chem. Today 2016, 34:16-19.

According to preferred embodiment of the invention Component A used in the process has the formula II (II)

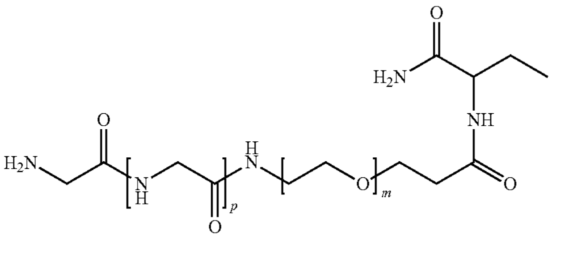

-continued

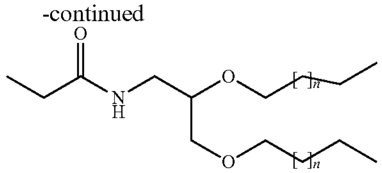

wherein m is any integer number from 15 to 60, preferably from 25 to 45, more preferably from 30 to 40 and is most preferably 36;

n is any integer number from 3 to 27, preferably from 7 to 19, more preferably from 11 to 15 and is most preferably 11;

p is any integer number from 0 to 9, preferably from 2 to 7, more preferably from 3 to 5 and is most preferably 4.

Therefore, the invention is also directed to a process wherein the component comprising the enzymatic tag, the hydrophilic spacer, the linker and the lipophilic moiety has the formula II, wherein m denotes 15 to 60;

n denotes 2 to 27;

p denotes 0 to 9.

In an especially preferred embodiment the process of the invention uses as Compound A a compound according to formula I, wherein n is 11, m is 36 and p is 4.

The conjugate obtained by the process of the invention is well suitable for the modification of lipid based drug delivery systems such as solid-lipid nanoparticles, nanoemulsions, micelles or liposomes, preferably liposomes. Therefore, the invention is also directed to the use of the conjugate obtained by the process for the modification of lipid based drug delivery systems such as solid-lipid nanoparticles, nanoemulsions, micelles or liposomes, preferably liposomes.

The term "nanoparticles" as used herein refers to particles having an average size of less than 1 μm. The nanoparticles preferably have a regular shape, such as spheres, but may also have an irregular shape.

The term "nanoemulsion" refers to a colloidal dispersion, typically a two-phase system of oil in water. The colloidal dispersion comprises droplets having an average size from 10 to 500 nm, preferably from 20 to 200 nm. The term "average size" or "mean size", as used herein, relates to the average diameter of the droplets.

The average size of these systems can be measured by standard processes known by persons skilled in the art such as dynamic light scattering.

The term "micelle" as used herein refers to an aggregate of amphiphilic molecules such as lipids, assembled so as to form a particle with a hydrophobic interior and a hydrophilic exterior. Micelles are generally spherical assemblies with diameters below 100 nm, although a range of micelle diameters and varying micelle shapes, such as discoid micelles, are known in the art.

The term "liposome" as used herein refers to a vesicle composed of one or more lipids, phospholipids and/or surfactants, which is useful for delivery of a drug (such as a chemotherapeutic agent) to a mammal. The components of the liposome is in a bilayer formation, similar to the lipid arrangement of biological membranes.

The conjugate obtained by the process of the invention is further well suitable for the modification of membranes of living cells, preferably T cells. Thus, the invention is further direct to the use of the conjugate obtained by the process for the modification of membranes of living cells, preferably T cells.

The term “T cells” as used herein, refers to a type of lymphocyte that matures in the thymus. T cells play an important role in cell-mediated immunity and are distinguished from other lymphocytes, such as B cells, by the presence of a T cell receptor on the cell surface. T cells may either be isolated (from spleen of animal origin or human blood donations) or obtained from a commercially available source. “T cell” includes all types of immune cells expressing CD3, including T-helper cells (CD4+ cells), cytotoxic T cells (CD8+ cells), natural killer T cells, T-regulatory cells (Treg) and gamma-delta T cells. A “cytotoxic cell” includes CD8+ T cells, natural-killer (NK) cells, and neutrophils, which cells are capable of mediating cytotoxicity responses.

The conjugate obtained by the process of the invention is further well suitable for the modification of surfaces with affinity towards hydrophobic substances, such as hydrophobic polystyrene. Accordingly, the invention is furthermore directed to the use of the conjugate obtained by the process for the modification of surfaces with affinity towards hydrophobic substances, such as hydrophobic polystyrene.

The term “hydrophobic” as used herein refers to the degree of affinity that a substance has with water. A hydrophobic substance substantially lacks affinity for water, tending to repel and not absorb water and tending not to dissolve in or mix with or be wetted by water.

Likewise, the conjugate obtained by the process of the invention is furthermore well suitable for the modification of membranes of exosomes so that the invention is also directed to the use of the conjugate obtained by the process for the modification of membranes of exosomes.

The term “exosome” as used herein refers to a cell-derived small (between 20-300 nm in diameter, more preferably 40-200 nm in diameter) vesicle comprising a membrane that encloses an internal space, and which is generated from said cell by direct plasma membrane budding or by fusion of the late endosome with the plasma membrane. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof. An exosome is a species of extracellular vesicle.

[1] D. Y. Lee, B.-H. Cha, M. Jung, A. S. Kim, D. A. Bull, Y.-W. Won, Cell surface engineering and application in cell delivery to heart diseases, Journal of Biological Engineering 12 (1) (2018) 28.

[2] L. Tang, Y. Zheng, M. B. Melo, L. Mabardi, A. P. Castaño, Y.-Q. Xie, N. Li, S. B. Kudchodkar, H. C. Wong, E. K. Jeng, M. V. Maus, D. J. Irvine, Enhancing T cell therapy through TCR-signaling-responsive nanoparticle drug delivery, Nature Biotechnology 36 (2018) 707.

[3] K. S. Lim, D. Y. Lee, G. M. Valencia, Y.-W. Won, D. A. Bull, Cell surface-engineering to embed targeting ligands or tracking agents on the cell membrane, Biochemical and Biophysical Research Communications 482 (4) (2017) 1042-1047.

[4] Y.-W. Won, A. N. Patel, D. A. Bull, Cell surface engineering to enhance mesenchymal stem cell migration toward an SDF-1 gradient, Biomaterials 35 (21) (2014) 5627-5635.

[5] N. Pishesha, A. M. Bilate, M. C. Wibowo, N.-J. Huang, Z. Li, R. Deshycka, D. Bousbaine, H. Li, H. C. Patterson, S. K. Dougan, T. Maruyama, H. F. Lodish, H. L. Ploegh, Engineered erythrocytes covalently linked to antigenic peptides can protect against autoimmune disease, Proceedings of the National Academy of Sciences 114 (12) (2017) 3157.

[6] N. Takemoto, Y. Teramura, H. Iwata, Islet Surface Modification with Urokinase through DNA Hybridization, Bioconjugate Chemistry 22 (4) (2011) 673-678.

[7] W.-y. Zhang, Y. Liu, Y. Wang, J. Nie, Y.-I. Guo, C.-m. Wang, H.-r. Dai, Q.-m. Yang, Z.-q. Wu, W.-d. Han, Excessive activated T-cell proliferation after anti-CD19 CAR T-cell therapy, Gene Therapy 25 (3) (2018) 198-204.

[8] S. Hacein-Bey-Abina, C. Von Kalle, M. Schmidt, M. P. McCormack, N. Wulffraat, P. Leboulch, A. Lim, C. S. Osborne, R. Pawliuk, E. Morillon, R. Sorensen, A. Forster, P. Fraser, J. I. Cohen, G. de Saint Basile, I. Alexander, U. Wintergerst, T. Frebourg, A. Aurias, D. Stoppa-Lyonnet, S. Romana, I. Radford-Weiss, F. Gross, F. Valensi, E. Delabesse, E. Macintyre, F. Sigaux, J. Soulier, L. E. Leiva, M. Wissler, C. Prinz, T. H. Rabbitts, F. Le Deist, A. Fischer, M. Cavazzana-Calvo, LMO2-Associated Clonal T Cell Proliferation in Two Patients after Gene Therapy for SCID-X1, Science 302 (5644) (2003) 415.

[9] M. Ruella, J. Xu, D. M. Barrett, J. A. Fraietta, T. J. Reich, D. E. Ambrose, M. Klichinsky, O. Shestova, P. R. Patel, I. Kulikovskaya, F. Nazimuddin, V. G. Bhoj, E. J. Orlando, T. J. Fry, H. Bitter, S. L. Maude, B. L. Levine, C. L. Nobles, F. D. Bushman, R. M. Young, J. Scholler, S. I. Gill, C. H. June, S. A. Grupp, S. F. Lacey, J. J. Melenhorst, Induction of resistance to chimeric antigen receptor T cell therapy by transduction of a single leukemic B cell, Nature Medicine 24 (10) (2018) 1499-1503.

[10] A. C. Braun, M. Gutmann, T. Lühmann, L. Meinel, Bioorthogonal strategies for site-directed decoration of biomaterials with therapeutic proteins, Journal of Controlled Release 273 (2018) 68-85.

[11] E. Saxon, C. R. Bertozzi, Cell Surface Engineering by a Modified Staudinger Reaction, Science 287 (5460) (2000) 2007.

[12] D. L. Iden, T. M. Allen, In vitro and in vivo comparison of immunoliposomes made by conventional coupling techniques with those made by a new post-insertion approach, Biochimica et Biophysica Acta (BBA)-Biomembranes 1513 (2) (2001) 207-216.

[13] S. Miura, Y. Teramura, H. Iwata, Encapsulation of islets with ultra-thin polyion complex membrane through poly (ethylene glycol)-phospholipids anchored to cell membrane, Biomaterials 27 (34) (2006) 5828-5835.

[14] T. Yamamoto, Y. Teramura, T. Itagaki, Y. Arima, H. Iwata, Interaction of poly(ethylene glycol)-conjugated phospholipids with supported lipid membranes and their influence on protein adsorption, Science and technology of advanced materials 17 (1) (2016) 677-684.

[15] A. Pulsipher, M. E. Griffin, S. E. Stone, J. M. Brown, L. C. Hsieh-Wilson, Directing Neuronal Signaling through Cell-Surface Glycan Engineering, Journal of the American Chemical Society 136 (19) (2014) 6794-6797.

[16] J. M. Antos, G. M. Miller, G. M. Grotenbreg, H. L. Ploegh, Lipid Modification of Proteins through Sortase-Catalyzed Transpeptidation, Journal of the American Chemical Society 130 (48) (2008) 16338-16343.

[17] S. E. Martin, B. R. Peterson, Non-Natural Cell Surface Receptors: Synthetic Peptides Capped with N-Cholesterylglycine Efficiently Deliver Proteins into Mammalian Cells, Bioconjugate Chemistry 14 (1) (2003) 67-74.

[18] M. G. Paulick, A. R. Wise, M. B. Forstner, J. T. Groves, C. R. Bertozzi, Synthetic Analogues of Glycosylphosphatidylinositol-Anchored Proteins and Their Behavior in Supported Lipid Bilayers, Journal of the American Chemical Society 129 (37) (2007) 11543-11550.

[19] U. Tomita, S. Yamaguchi, Y. Maeda, K. Chujo, K. Minamihata, T. Nagamune, Protein cell-surface display through in situ enzymatic modification of proteins with a poly(Ethylene glycol)-lipid, Biotechnology and Bioengineering 110 (10) (2013) 2785-2789.

[20] D. Y. Lee, K. S. Lim, G. M. Valencia, M. Jung, D. A. Bull, Y.-W. Won, One-Step Method for Instant Generation of Advanced Allogeneic NK Cells, Advanced science 5 (11) (2018) 1800447-1800447.

[21] M. Ritzefeld, Sortagging: A Robust and Efficient Chemoenzymatic Ligation Strategy, Chemistry—A European Journal 20 (28) (2014) 8516-8529.

[22] J. E. Glasgow, M. L. Salit, J. R. Cochran, In Vivo Site-Specific Protein Tagging with Diverse Amines Using an Engineered Sortase Variant, Journal of the American Chemical Society 138 (24) (2016) 7496-7499.

[23] S. A. van Lith, S. M. van Duijnhoven, A. C. Navis, W. P. Leenders, E. Dolk, J. W. Wennink, C. F. van Nostrum, J. C. van Hest, Legomedicine-A Versatile Chemo-Enzymatic Approach for the Preparation of Targeted Dual-Labeled Llama Antibody-Nanoparticle Conjugates, Bioconjug Chem 28 (2) (2017) 539-548.

[24] L. Bourel-Bonnet, H. Gras-Masse, O. Melnyk, A novel family of amphilic α-oxo aldehydes for the site-specific modification of peptides by two palmitoyl groups in solution or in liposome suspensions, Tetrahedron Letters 42 (39) (2001) 6851-6853.

[25] R. M. Epand, Biophysical studies of lipopeptide-membrane interactions, Peptide Science 43 (1) (1997) 15-24.

[26] D. Kirpotin, J. W. Park, K. Hong, S. Zalipsky, W. L. Li, P. Carter, C. C. Benz, D. Papahadjopoulos, Sterically stabilized anti-HER2 immunoliposomes: design and targeting to human breast cancer cells in vitro, Biochemistry 36 (1) (1997) 66-75.

[27] T. Nagamune, C. Itoh, T. Yasukohchi, S. Ohhashi, K. Kubo, Cell having modified cell membrane, Google Patents, 2007.

[28] L. K. Swee, S. Lourido, G. W. Bell, J. R. Ingram, H. L. Ploegh, One-Step Enzymatic Modification of the Cell Surface Redirects Cellular Cytotoxicity and Parasite Tropism, ACS Chemical Biology 10 (2) (2015) 460-465.

[29] S. Wöll, C. Bachran, S. Schiller, M. Schröder, L. Conrad, L. K. Swee, R. Scherließ, Sortaggable liposomes: Evaluation of reaction conditions for single-domain antibody conjugation by Sortase-A and targeting of CD11b+ myeloid cells, European Journal of Pharmaceutics and Biopharmaceutics 133 (2018) 138-150.

[30] T. Ishida, D. L. Iden, T. M. Allen, A combinatorial approach to producing sterically stabilized (Stealth) immunoliposomal drugs, FEBS letters 460 (1) (1999) 129-133.

[31] P. Marques-Gallego, A.I.P.M. de Kroon, Ligation Strategies for Targeting Liposomal Nanocarriers, BioMed Research International 2014 (2014) 12.

[32] M. Oswald, S. Geissler, A. Goepferich, Determination of the activity of maleimide-functionalized phospholipids during preparation of liposomes, International journal of pharmaceutics 514 (1) (2016) 93-102.

[33] G. T. Noble, J. F. Stefanick, J. D. Ashley, T. Kiziltepe, B. Bilgicer, Ligand-targeted liposome design: challenges and fundamental considerations, Trends in Biotechnology 32 (1) (2014) 32-45.

[34] X. Guo, Z. Wu, Z. Guo, New method for site-specific modification of liposomes with proteins using sortase A-mediated transpeptidation, Bioconjug Chem 23 (3) (2012) 650-5.

[35] J. R. Silvius, R. Leventis, A Novel "Prebinding" Strategy Dramatically Enhances Sortase-Mediated Coupling of Proteins to Liposomes, Bioconjugate Chemistry 28 (4) (2017) 1271-1282.

[36] A. Tabata, N. Anyoji, Y. Ohkubo, T. Tomoyasu, H. Nagamune, Investigation on the Reaction Conditions of *Staphylococcus aureus* Sortase A for Creating Surface-modified Liposomes as a Drug-delivery System Tool, Anticancer Research 34 (8) (2014) 4521-4527.

[37] A. Tabata, Y. Ohkubo, N. Anyoji, K. Hojo, T. Tomoyasu, Y. Tatematsu, K. Ohkura, H. Nagamune, Development of a Sortase A-mediated Peptide-labeled Liposome Applicable to Drug-delivery Systems, Anticancer Research 35 (8) (2015) 4411-4417.

[38] S. Wöll, S. Schiller, C. Bachran, L. K. Swee, R. Scherließ, Pentaglycine lipid derivates—rp-HPLC-analytics for bioorthogonal anchor molecules in targeted, multiple-composite liposomal drug delivery systems, International Journal of Pharmaceutics (2018).

The examples illustrate the invention without being restricted thereto.

Methods

For expression of the proteins the method described by Bachran et al. was used (Bachran, M. et al.: The activity of myeloid cell-specific VHH immunotoxins is target-, epitope-, subset- and organ dependent, Scientific Reports 7(1) (2017) 17916).

For this VHHs, and recombinant SrtA28 were expressed in *E. coli* strains WK6 (VHHs) and BL21 (DE3) (SrtA expression). Expression cultures in terrific broth (12 g/L tryptone, 24 g/L yeast extract, 5 g/L glycerol, 2.3 g/L KH2PO4, 12.5 g/L K2HPO4) in the presence of suitable antibiotics were grown at 37° C. to an OD600 nm of 0.8. Isopropyl β-D-thiogalactopyranoside (BioChemica, # A1008,0025) was added to a final concentration of 1 mM and cultures were incubated for a further 3 hours at 37° C. Cells were harvested by centrifugation (15 min, 4000×g, 4° C.), the pellets resuspended in 20 mL PBS (150 mM NaCl, 8.3 mM Na2HPO4, 1.7 mM KH2PO4, pH 7.4)/400 mL culture. Resuspended samples were lysed by sonication (2×1 min sonication, 100% intensity, 50% duty cycle, Sonicator HD2070, Sonotrode KE76, Bandelin), centrifuged (30 min, 38000×g, 4° C.) and the supernatants applied to nickel-nitrilotriacetic acid agarose (Protino Ni-NTA, Macherey-Nagel) columns. All expressed proteins contain a 6× His-tag, allowing the purification of proteins by metal chelate-chromatography. The columns were washed subsequently by PBS, PBS+20 mM imidazole, and PBS+50 mM imidazole. Proteins were eluted by PBS+250 mM imidazole. The eluted proteins were concentrated in Amicon centrifugal filter devices (Millipore) with a 3 kDa cutoff (for VHHs) and 10 kDa cutoff (for SrtA). The concentrated proteins were dialyzed overnight against PBS. The concentration of dialyzed proteins was determined by absorbance measurements at 280 nm. The purity of the purified proteins was analyzed by reducing SDS-PAGE (12% gel) and Coomassie staining. The final material was determined to be >90% pure.

The absorption coefficients were based on the primary protein sequence and calculated from the online software ExPASy ProtParam, SIB, Lausanne, Switzerland.

Sequences of the utilized proteins (1-letter code according to Nomenclature and symbolism for amino acids and peptides (Recommendations 1983), Pure and Applied Chemistry, 1984, p. 595])

```
Sortase A (SrtA7m)
                                            [SEQ ID NO 1]
MGHHHHHHSSGLVPRGSGMKETAAAKFERQHMDSPDLGTQAKPQIPKDKS

KVAGYIEIPDADIKEPVYPGPATREQLNRGVSFAKENASLDDQNISIAGH

TFIDRPNYQFTNLKAAKKGSMVYFKVGNETRKYKMTSIRNVKPTAVEVLD

EQKGKDKQLTLITCDDYNEETGVWETRKIFVATEVK

VHH DC13
                                            [SEQ ID NO 2]
QVQLQESGGGLVQAGGSHNLSCTASGITFSSLAMGWFRQTPGKEREFVAN

IMRSGSSVFYADSVRGRFTISRDNAKNTAHLQMNSLKPEDTAVYFCAATR

GAWPAEYWGQGTQVTVSSGGLPETGGHHHHHH

VHH ENH
                                            [SEQ ID NO 3]
QVQLQESGGALVQPGGSLRLSCAASGFPVNRYSMRWYRQAPGKEREWVAG

MSSAGDRSSYEDSVKGRFTISRDDARNTVYLQMNSLKPEDTAVYYCNVNV

GFEYWGQGTQVTVSSGGLPETGGHHHHHH

eGFP (enhanced green fluorescent protein)
                                            [SEQ ID NO 4]
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKHHHHHH
```

DMA-PEG-G5

DMA-PEG-G5 is a substance having the formula shown in FIG. 1.

EXAMPLE 1

Stock of structure 2, in FIG. 1, further called here DMA-PEG-G5 (25 mg/mL in chloroform) was aliquoted in a HPLC vial. Chloroform was evaporated under a gentle stream of nitrogen creating a thin lipid film, which was hydrated with DPBS (Dulbecco's phosphate buffered saline, Sigma Aldrich, # D1408) pH 7.4 as micellar aqueous lipid dispersion (2 mM). Alternatively, DMA-PEG-G5 was dissolved in DPBS pH 7.4 (5-10 mg/mL) using ultrasound. 400 μL of 50 μM VHH, 25 μM Sortase-A and 1 mM DMA-PEG-G5, which corresponded to a target product mass of 320 μg, were incubated for 4 h at 4° C., until the conjugate was isolated using reversed-phase HPLC (rp-HPLC). Reaction bulk and product were separated utilizing an Aeris Widepore C4 column (3.6 μm particle size, 100 mm length, 2.1 mm diameter, Waters Corporation, Milford, Massachusetts, USA) and a binary gradient pattern (Table).

TABLE 2 rp-HPLC gradient pattern for separation of reaction bulk and product (A: water with 0.1% trifluoroacetic acid (TFA v/v; B: acetonitrile with 0.05 % TFA v/v)

| time [min] | solvent composition |
|---|---|
| 0 | 95% A |
| 5.5 | 45.5% A |
| 15 | 18.5% A |
| 15.1 | 5% A |
| 18 | 5% A |
| 18.1 | 95% A |
| 20 | 95% A |

Eluent A was water with 0.1% TFA, eluent B was acetonitrile with 0.05 TFA. Analysis was performed on an Agilent 1110 HPLC system equipped with a degasser, binary pump, temperature controlled autosampler, column oven, diode array detector (DAD) and an analytical fraction collector (AFC), controlled by EZChrom Elite Software (Agilent Technologies, Santa Clara, CA, USA). Column temperature was set to 30° C., autosampler temperature was 4° C. Standard analytical or isolation injection volume was 5 μL or 25-100 μL, respectively. Flow rate was 0.5 mL/min. Data was recorded using DAD at 214 and 280 nm.

The conjugate peak was collected either manually or using an automated fraction collector. Collections of single injections were stored on ice, until the eluent mixture was removed using a vacuum centrifuge (RVC 2-33 IR, Martin Christ, Osterode am Harz, Germany; speed: 1500 rpm; temperature: 40° C.; 100 mbar for 10 min, followed by 20 mbar for 20 min and further evaporation at 2 mbar). The resulting pellet was hydrated with water, and protein concentrations were determined by UV spectroscopy (NP80, Implen, Westlake Village, CA, USA) using extinction coefficients calculated by ExPASy ProtParam web application (https://web.expasy.org/protparam, SIB, Lausanne, Switzerland). Yield was calculated based on the mass and concentration of the recovered protein solution and the target product mass. Purity was determined by rp-HPLC analysis at 214 nm with automated peak detection between 2-15 min and a threshold level obtained from background noise of a water blank.

To verify the reaction product, the method was transferred to a similar HPLC system equipped with an electrospray ionization mass spectrometer (ESI-MS, amaZon SL, Bruker Corporation, Billerica, Massachusetts, USA). Ion source type was set to ESI with positive polarity. Capillary exit was 140 V, trap drive was set to "94". The mass range mode was set to enhanced resolution, with a scanning range from 100-2200 m/z. 5 spectra were averaged per run. Masses were calculated using deconvolution of raw spectra.

EXAMPLE 2

The isolated VHH ENH conjugate from Example 1 or native VHH ENH (100 nM) was spiked to 100 nM eGFP. VHH ENH is known for its ability to increase the intrinsic fluorescence of eGFP upon binding. Increase in fluorescence intensity compared to sole eGFP was measured in a black 96-well plate (Thermo Fisher Scientific, Waltham, Massachusetts, USA) utilizing a Spark Plate Reader (Tecan Group, Männedorf, Switzerland) with excitation and emission set to 485 nm and 535 nm, respectively.

EXAMPLE 3

FITC-dextran (fluorescein isothiocyanate) labelled liposomes were prepared as described elsewhere [4]. In brief, a mixture of DPPC (1,2-dipalmitoylphosphatidylcholine) cholesterol, DPPG (1,2-Dipalmitoyl-phosphatidylglycerole) and DMA-PEG-G5 (59.4:34.6:5.0:1.0, molar fractions) was dissolved to 32 mM in methanol and injected via a computer-controlled binary pumping system into a 10 mg/mL FITC (fluoresceine isothiocyanate) dextran solution in DPBS pH 7.4 utilizing a customized T-piece with a 27G needle. The dispersion was purified and concentrated by tangential flow filtration. Lipid concentration was determined by an rp-HPLC method with evaporative light scattering detection described elsewhere [5]. To prepare immunoliposomes, the lipidated VHH ENH or VHH DC13 were added to the liposomal dispersion to 0.25-2 nM VHH per μM phospholipid (PL). The mixture was thoroughly vortexed and incubated at 50° C. for 30 min.

Murine myeloid-derived suppressor CD11b+Gr-1+ cells (MDSC) were derived from bone marrow-derived NUP-progenitor cells [6]. MDSC were differentiated for four days in complete RPMI (RPMI 1640 medium, Life Technologies, #21875-034, Carlsbad, CA, USA) supplemented with 10% heat-inactivated fetal bovine serum, 100 U/mL penicillin (Life Technologies, #15140122), 100 μg/mL streptomycin (Life Technologies, #15140122), 1 mM sodium pyruvate (Life Technologies, #11360070), 50 μM 2-mercaptoethanol (Life Technologies, #31350-010), and 1×non-essential amino acids (Life Technologies, #11140-035) supplemented with 20 ng/mL interleukine-6 and 20 ng/mL granulocyte-macrophage colony-stimulating factor (Biolegend, #576304, San Diego, USA). To investigate binding of VHH-modified liposomes, MDSC were incubated with 500 μM of the liposomes (based on total lipid content) for 4 h at 4° C. Cells were washed with FACS buffer (1×PBS+2% heat-inactivated fetal bovine serum) and antibody staining of cells was performed in presence of Fc receptor block (TruStain FcX, BioLegend, #422302) in FACS buffer. SytoxBlue (Thermo Fisher Scientific, S34857) was used for exclusion of dead cells. Liposomes were detected via encapsulated FITC-dextran.

EXAMPLE 4

T cells were isolated from spleens of C57BU6j mice maintained under specific pathogen-free conditions at the animal facility of the University of Heidelberg and euthanized under the registered protocol T47/16. Spleens were mashed and CD8+ cells isolated after red cell lysis (ACK lysing buffer, #A1049201, Thermo Fisher Scientific) using a mouse CD8a+ T cell isolation kit (#130-104-075, Miltenyi Biotec, Bergisch-Gladbach, Germany) and magnetic cell isolation (LS columns, #130-042-401, Miltenyi Biotec) used according to manufacturer's instructions. Purified CD8+ T cells were stained by 1 nM Cell Tracer Far Red (#C34564, Thermo Fisher Scientific) for 5 min at 35° C. and washed with FACS buffer. Stained T cells (1.65×108 cells/mL) were incubated with 650 nM native or lipidated VHH DC13 and VHH ENH for 1 h at 4° C. Lipidated VHH binding to T cells was detected by an FITC-anti-llama antibody.

Murine myeloid-derived suppressor CD11b+Gr-1+ cells (MDSC) were derived from bone marrow-derived NUP-progenitor cells [6]. MDSC were differentiated for four days in complete RPMI (RPMI 1640 medium, Life Technologies, #21875-034, Carlsbad, CA, USA) supplemented with 10 heat-inactivated fetal bovine serum, 100 U/mL penicillin (Life Technologies, #15140122), 100 μg/mL streptomycin (Life Technologies, #15140122), 1 mM sodium pyruvate (Life Technologies, #11360070), 50 μM 2-mercaptoethanol (Life Technologies, #31350-010), and 1×non-essential amino acids (Life Technologies, #11140-035) supplemented with 20 ng/mL interleukine-6 and 20 ng/mL granulocyte-macrophage colony-stimulating factor (Biolegend, #576304, San Diego, USA). To investigate membrane insertion of lipidated VHHs, MDSC ($10^7$cells/mL) were incubated for 30 min at 4° C. with 500 nM of native or lipidated VHH ENH or VHH DC13. Cells were washed with FACS buffer (1×PBS+2% heat-inactivated fetal bovine serum) and antibody staining of cells was performed in presence of Fc receptor block (TruStain FcX, BioLegend, #422302) in FACS (fluorescence assisted cell sorting) buffer. SytoxBlue (Thermo Fisher Scientific, S34857) was used for exclusion of dead cells. Lipidated VHH inserted into the cell membrane was detected by a FITC-anti-llama antibody (Invitrogen, #A16061). All analyses of cells were performed by flow cytometry. Flow cytometry was performed on a FACSAria II (Beckton, Dickinson and Company, Franklin Lakes, NJ, USA) and results were analyzed by FlowJo (Tree Star, V.10.0.8).

EXAMPLE 5

CD11b+Gr-1+ cells from example 4 were incubated with 100 μg/mL eGFP at 4° C. for 30 min to detect binding of eGFP to lipidated VHH ENH being inserted into the cell membrane. Flow cytometry was performed on a FACSAria II (Beckton, Dickinson and Company, Franklin Lakes, NJ, USA) for fluorescence of eGFP, results were analyzed by FlowJo (Tree Star, V.10.0.8).

EXAMPLE 6

For cell-cell interaction experiments, T cells were isolated from spleens of C57BL/6j mice maintained under specific pathogen-free conditions at the animal facility of the University of Heidelberg and euthanized under the registered protocol T47/16. Spleens were mashed and $CD8^+$ cells isolated after red cell lysis (ACK lysing buffer, #A1049201, Thermo Fisher Scientific) using a mouse $CD8a^+$ T cell isolation kit (#130-104-075, Miltenyi Biotec, Bergisch-Gladbach, Germany) and magnetic cell isolation (LS columns, #130-042-401, Miltenyi Biotec) used according to manufacturer's instructions. Purified $CD8^+$ T cells were stained by 1 nM Cell Tracer Far Red (# C34564, Thermo Fisher Scientific) for 5 min at 35° C. and washed with FACS buffer. Stained T cells ($1.65\times10^8$ cells/mL) were incubated with 650 nM native or lipidated VHH DC13 and VHH ENH for 1 h at 4° C. VHH-labeled T cells were washed twice with FACS buffer and $3\times10^7$ T cells were incubated with $1.1\times10^7$ MDSC (obtained as described in example 4) for 1 h at 4° C. T cells and MDSC were loaded on LS columns for magnetic bead isolation of $CD8^+$ T cells and co-purification of MDSC bound to T cells. Eluted cells were stained by anti-CD11b-Brilliant Violet 605 and anti-Gr-1-FITC (#101237 and #108405, Biolegend) and analyzed by flow cytometry as described above.

EXAMPLE 7

Native or lipidated VHH ENH (batch #3 of example 1) were mixed with eGFP in DPBS pH 7.4 (1×, Sigma, # D1408) in different variations in a ThermoFisher Polysorp 96-well plate (# Nunc 475094). The variations included: PBS, PBS with eGFP (50 nM), PBS with eGFP (50 nM)+ native VHH ENH (50 nM), PBS with eGFP (50 nM)+ lipidated VHH ENH (5-50 nM). The plates were incubated at 60 rpm, 37° C. for 1.5 h in an orbital shaker. Afterwards, the plate was centrifugated for 1 min@300 g to collect all liquid at the bottom of the well. The plate was then measured using TecanReader Spark (ThermoFischer) with an excitation of 485 nm and emission of 525 nm. Afterwards, the liquid in the wells was exchanged for 5 times. After each the 1., 2., 3. and 5. exchange step, fluorescence was measured.

Surprisingly, it has been found that a compound composed of an enzymatic tag, an hydrophilic spacer, a linker and a lipophilic moiety (Structure 2 in FIG. 1) can be dissolved in aqueous buffers up to 10 mg/mL (4 mM) (Example 1).

After preparation of a mixture of 1 mM of Structure 2, 25 μM of the transpeptidase sortase A and 50 μM of an LPETG-modified singe-domain antibody (Example 1) (Structure 1), an efficient lipidation of structure 1 was observed after 4 h after analysis by reversed phase HPLC (FIG. 3, exemplary chromatogram for VHH ENH utilized as structure 1).

Additionally, no aggregation or precipitation of the lipidated product was observed during the reaction as analyzed via visual inspection (Example 1).

Mass spectrometry confirmed the expected molecular masses for two different single-domain antibodies (VHH ENH (FIG. 4), VHH DC13 (FIG. 5), (Example 1).

The reaction bulk was purified by collecting the column effluent of the described reversed phase HPLC method of the "lipidated VHH" peak in a glass vial. The eluent mixture composed of water, acetonitrile and trifluoroacetic acid was removed by vacuum centrifugation. The so obtained pellet was could be dissolved in water to ~1 mg/mL protein content (Example 1).

The purity of the so obtained lipidated single-domain antibodies was analysed via reversed phase HPLC combined with UV detection at 214 nm. It revealed purities above >95% (based on the UV area) for following batches (FIG. 6, Table 1) (Example 1).

TABLE 1

| conjugate | purity [area %] | yield |
|---|---|---|
| VHH ENH lot #1 | 96% | 50% |
| VHH ENH lot #2 | 97% | 52% |
| VHH ENH lot #3 | 95% | 27% |
| VHH DC13 lot #1 | 97% | 60% |

The yield was calculated based on the mass and concentration of the recovered protein solution and the target product mass (320 μg protein per batch). Good yields >50% were obtained, except for VHH ENH lot #3, which was prepared without cooling the column effluent (Example 1).

The biological activity of the via reversed phase HPLC purified conjugates was analyzed by the ability of the lipidated VHH ENH to increase the fluorescence of eGFP upon binding (Example 2) [1].

Three different batches were incubated with with eGFP and the fluorescence intensity at 485 nm excitation and 535 nm emission was compared to that of native VHH ENH. The data revealed no losses of binding in lot #1 and lot #2 (FIG. 7) (Example 2). Lo t#3 was prepared without cooling the column effluent and showed slightly decreased fluorescence enhancement of eGFP (Example 2).

The lipidated and isolated single-domain antibodies VHH ENH and VHH DC13 were incubated with FITC-labelled liposomal drug delivery systems (Example 3) in different ratios of VHH to phospholipid. The via this post-insertion process modified liposomes were then incubated with cultured murine CD11b+Gr-1+ cells. VHH DC13 binds to the cellular surface receptor CD11b, and VHH DC13-modified liposomes showed a clear cellular association with the CD11b+Gr-1+ cells during flow cytometry analysis (FIG. 8, shows data for VHH DC13 surface density on the liposomes of 2 nM/μM phospholipid, percentage in each dot plot indicates number of positive cell in the marked gate. FSC: forward scatter) (Example 3).

When the liposomes were incubated with different ratios of lipidated VHH DC13 to the phospholipid concentration, an optimum of binding on the cells was observed for 0.5 nM VHH DC13 per μM phospholipid (FIG. 8) (Example 3).

To assess whether the lipidated VHHs can be used for cell membrane remodelling, CD11b+Gr-1+ cells or T cells were incubated with lipidated or native VHH ENH or VHH DC13 (Example 4). After washing of cells, VHH presence on the cellular surface was confirmed by flow cytometry after staining the cells with an FITC-anti-llama antibody (Example 4, FIG. 10). Lipidated VHHs clearly increase the fluorescence signal obtained from the cells in flow cytometry (Example 4). If VHH DC13 was incubated with CD11b+ cells, no differences between lipidated and non-lipidated form was detected, since the direct binding of VHH DC13 to CD11b overrides the hydrophobic insertion effect (Example 4).

To assess whether the lipidated VHHs present on the cellular surface are also accessible for soluble antigens, CD11b+Gr-1+ cells were incubated with lipidated or native VHH ENH or VHH DC13 (Example 5). After cell washing, the cells were incubated with the for VHH ENH corresponding antigen eGFP. Flow cytometry revealed a selective capturing of eGFP by cells which had been treated with the lipidated VHH ENH (Example 5, FIG. 11).

To assess whether the lipidated VHHs present on the cellular surface are also able to promote a cell-cell interaction (Example 6), isolated CD8+ T cells were incubated with lipidated or native VHH ENH or VHH DC13. Afterwards, the so modified cells were incubated with CD11b+Gr-1+ cells. This cell mixture was firstly separated by magnetic bead assisted cell sorting specific for the antigen CD8. Afterwards, $CD8^+$ retentate was stained for CD11b and Gr-1 and analyzed by flow cytometry (FIG. 14) (Example 6). Cellular populations pre-incubated with lipidated VHH DC13 caused higher signals for MDSC in the CD8-positive column retentate, indicating a VHH promoted cellular interaction between MDSC and T cells (FIG. 13) (Example 6).

To assess whether lipidated VHHs can be immobilized on hydrophobic surfaces such as hydrophobic polystyrene, lipidated or native VHH ENH were incubated in presence of 50 nM eGFP (the corresponding antigen of VHH ENH) in a Polysorp® 96-well plate (Example 7). After several washing steps, a significant coating and retention eGFP was observed in the wells for 25 nM and 50 nM coating (FIG. 14). The data indicates usability of the lipidated VHHs for antigen or cell capturing or immobilization on cells (Example 7). It could also be used for purification of proteins.

SEQUENCE LISTING

Figure 1:
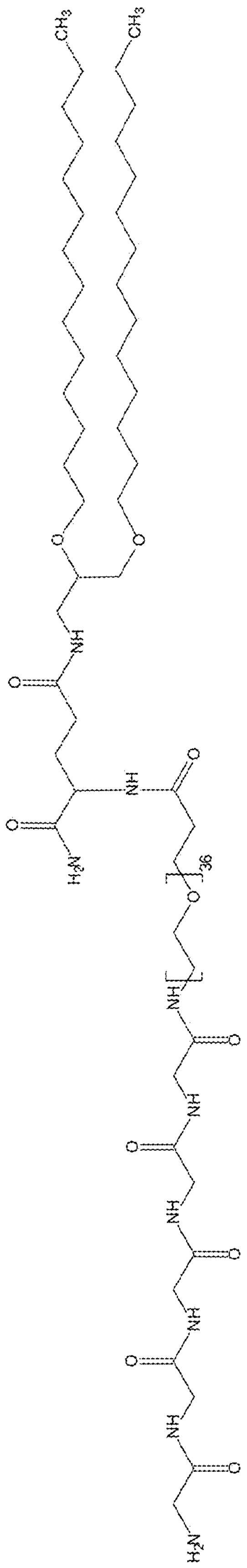
FIG. 1 illustrates the structure of DMA-PEG-GS.
Figure 2:
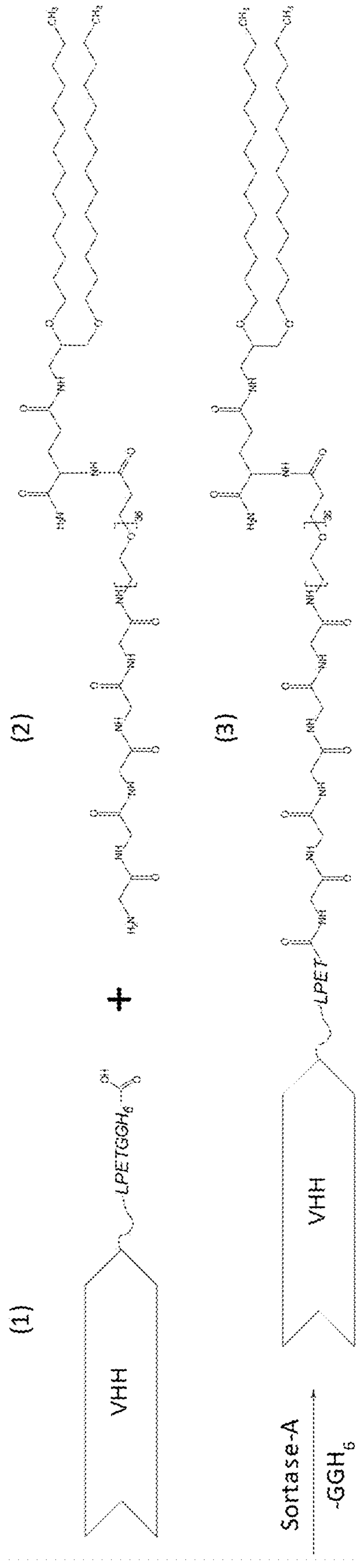
FIG. 2 illustrates a reaction scheme.
Figure 3:
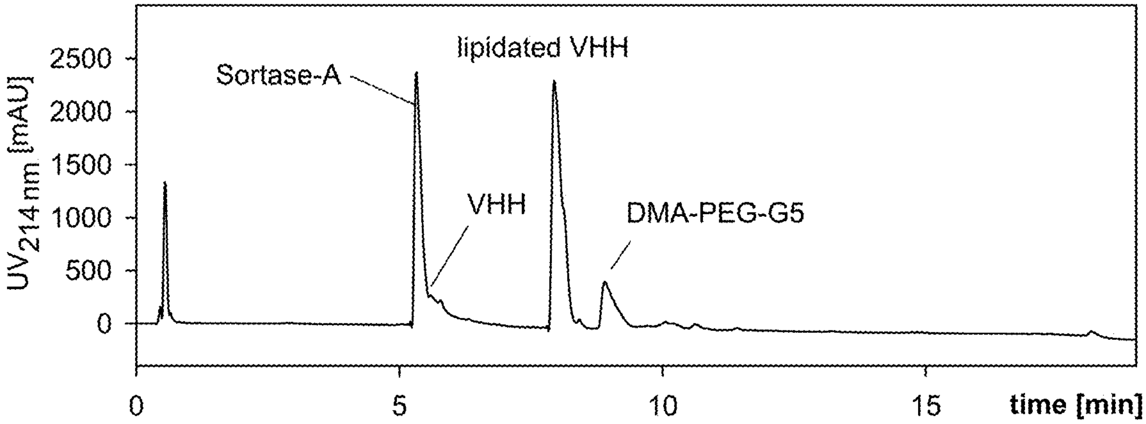
FIG. 3 illustrates an exemplary chromatogram for VHH ENH utilized as structure 1.
Figure 4:
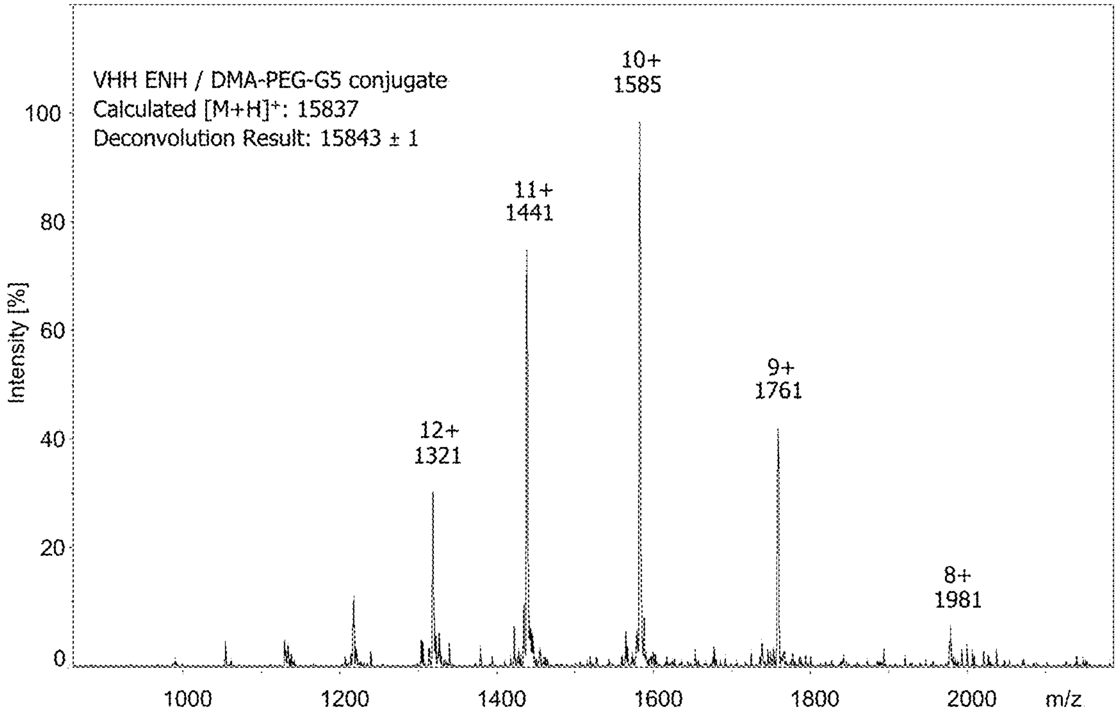
FIG. 4 illustrates mass spectrometry confirming the expected molecular mass of the single-domain antibody VHH ENH.
Figure 5:
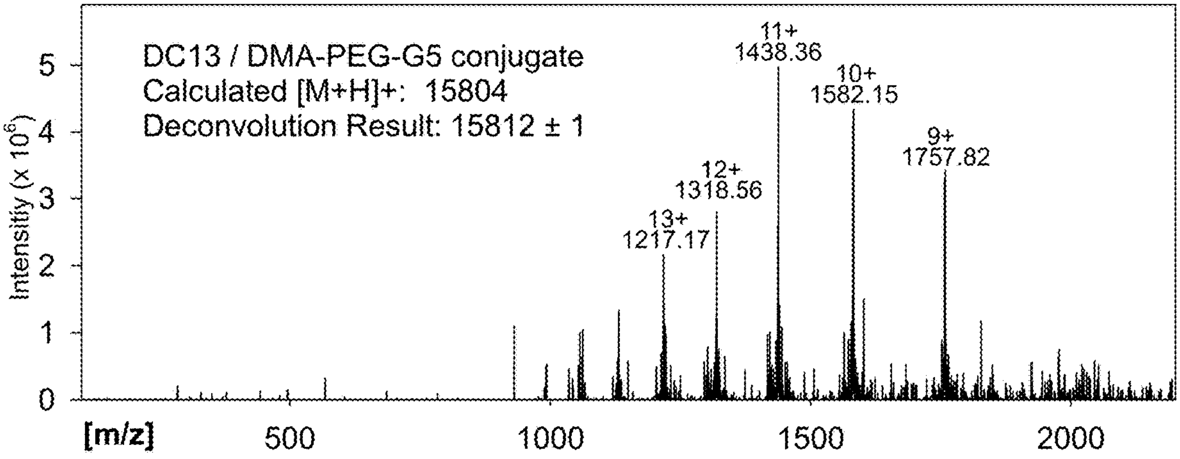
FIG. 5 illustrates mass spectrometry confirming the expected molecular mass of the single-domain antibody VHH DC13.
Figure 6:
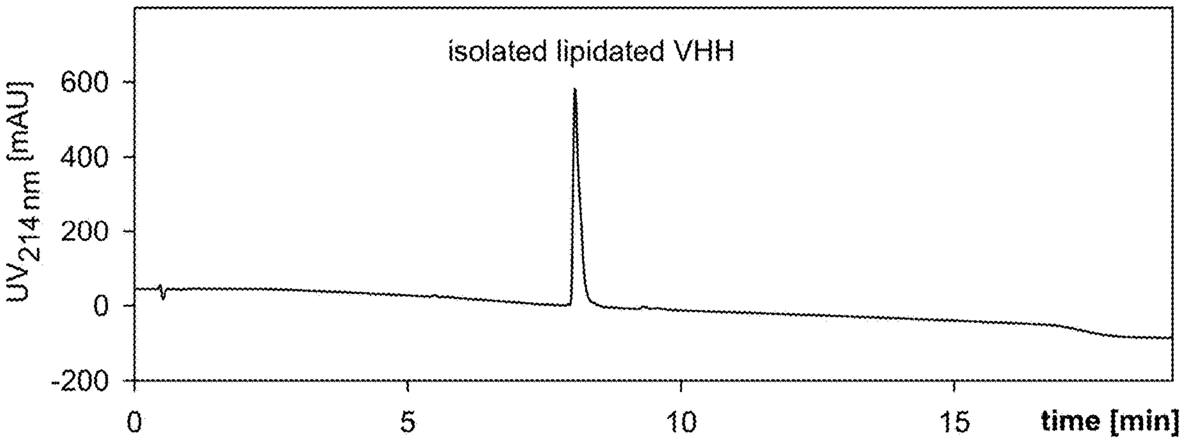
FIG. 6 illustrates reversed phase HPLC combined with UV detection at 214 nm revealing purities above >95% based on the UV area for batches from Table 1.
Figure 7:
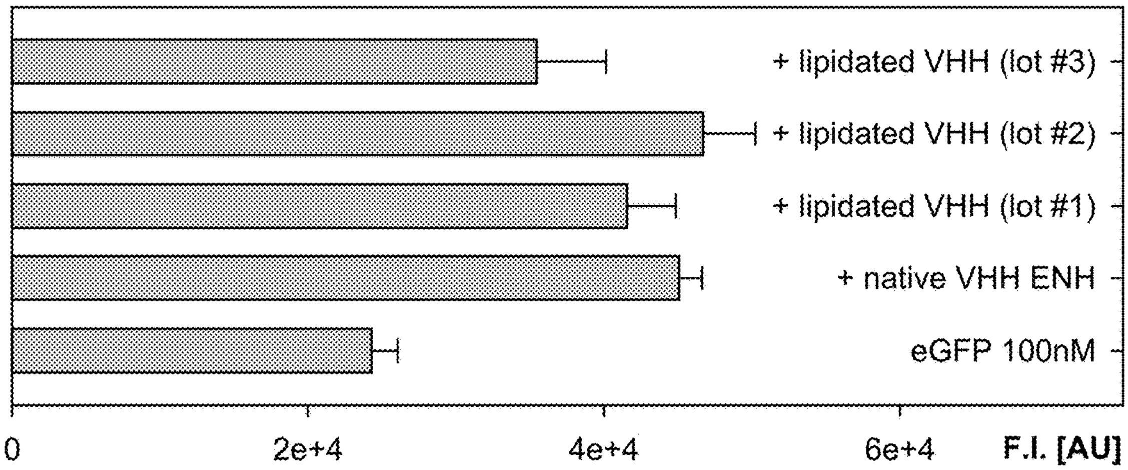
FIG. 7 illustrates data revealing no losses of binding in lot #f1 and lot #2 and for Lot #3 showing slightly decreased fluorescence enhancement of eGFP.
Figure 8:
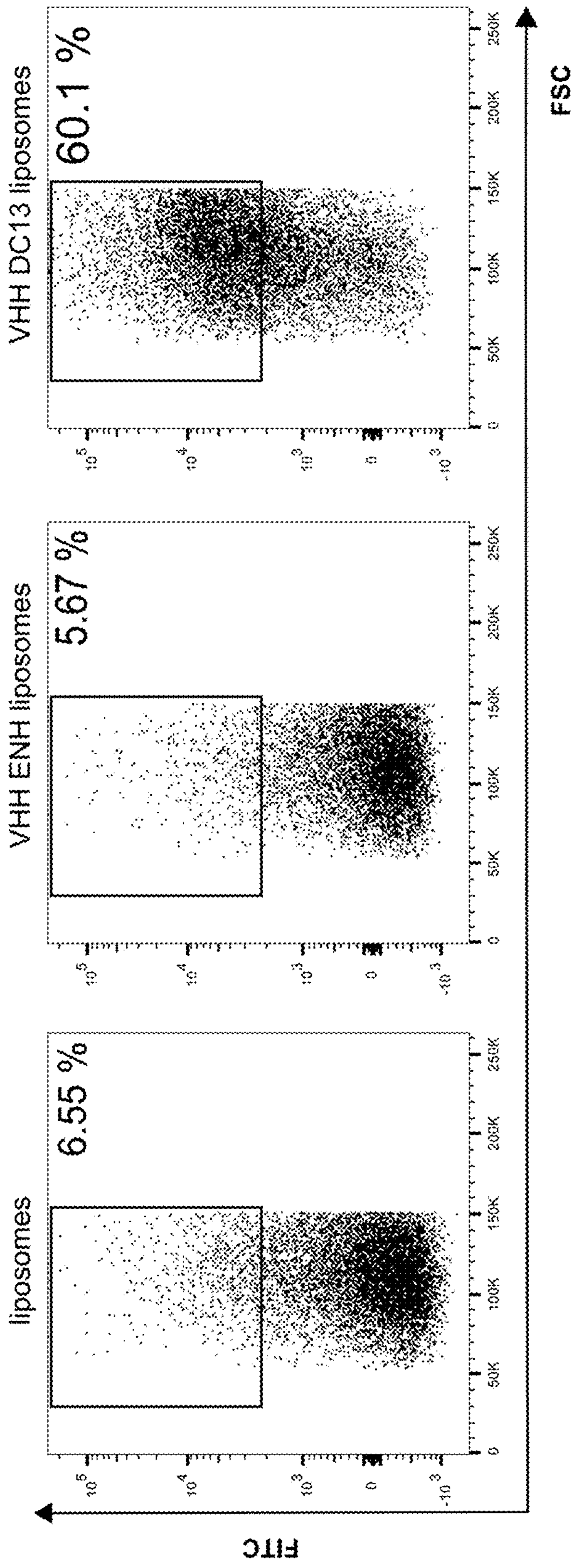
FIG. 8 illustrates data for VHH DC13 surface density on the liposomes of 2 DM/AM phospholipid.
Figure 9:
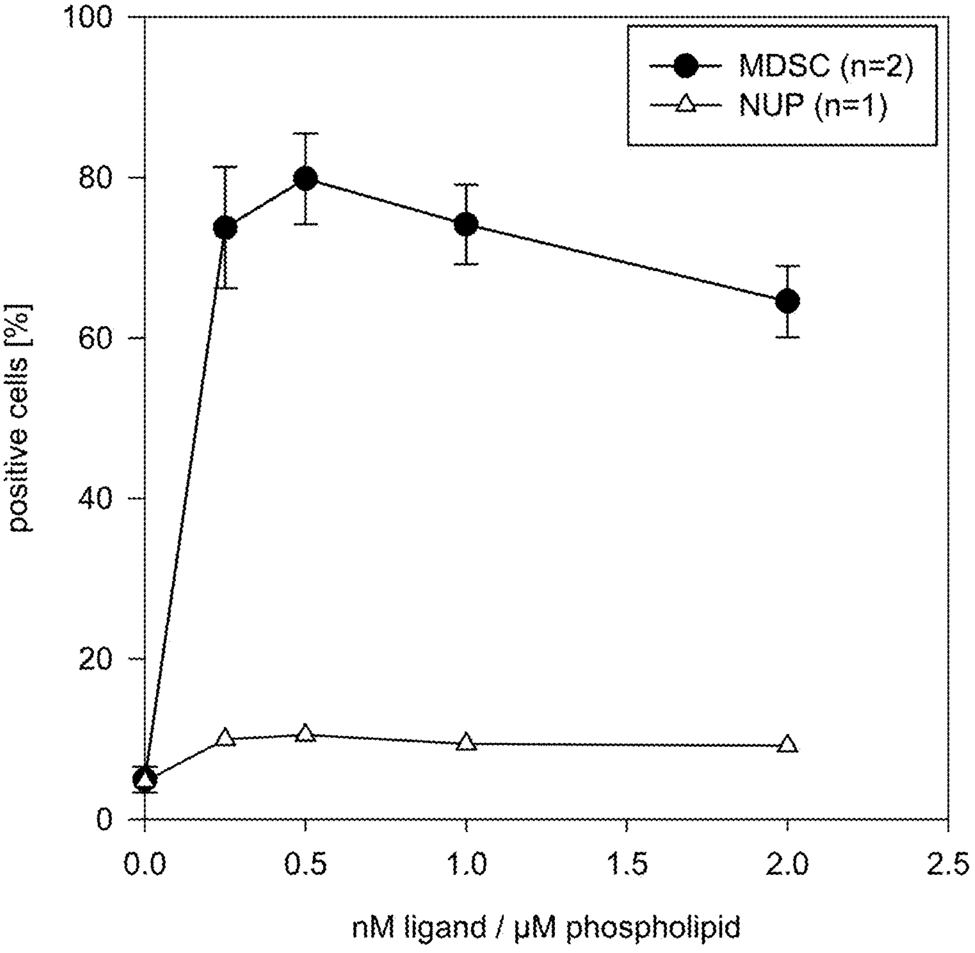
FIG. 9 illustrates that when liposomes were incubated with different ratios of lipidated VHH DC13 to the phospholipid concentration, an optimum of binding on the cells was observed for 0.5 nM VHH DC13 per μM phospholipid.
Figure 10:
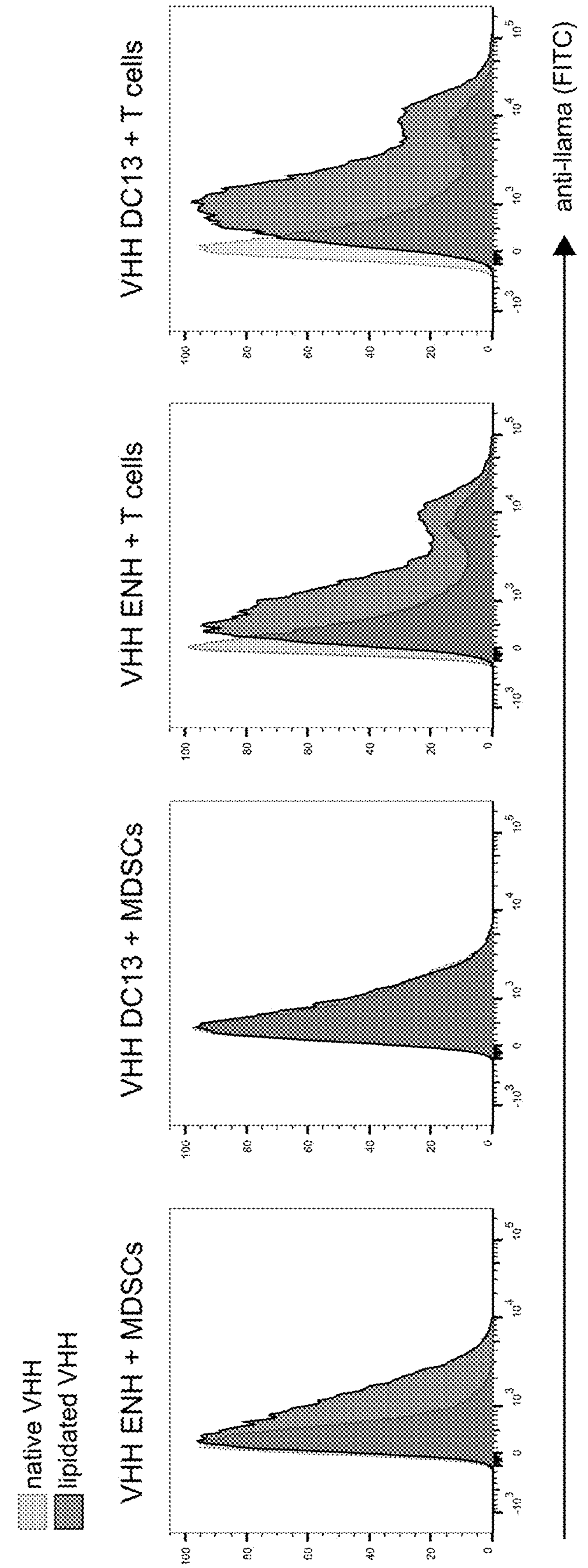
FIG. 10 illustrates the confirmation of the presence on the cellular surface by flow cytometry after staining the cells with an FITC-anti-llama antibody.
Figure 11:
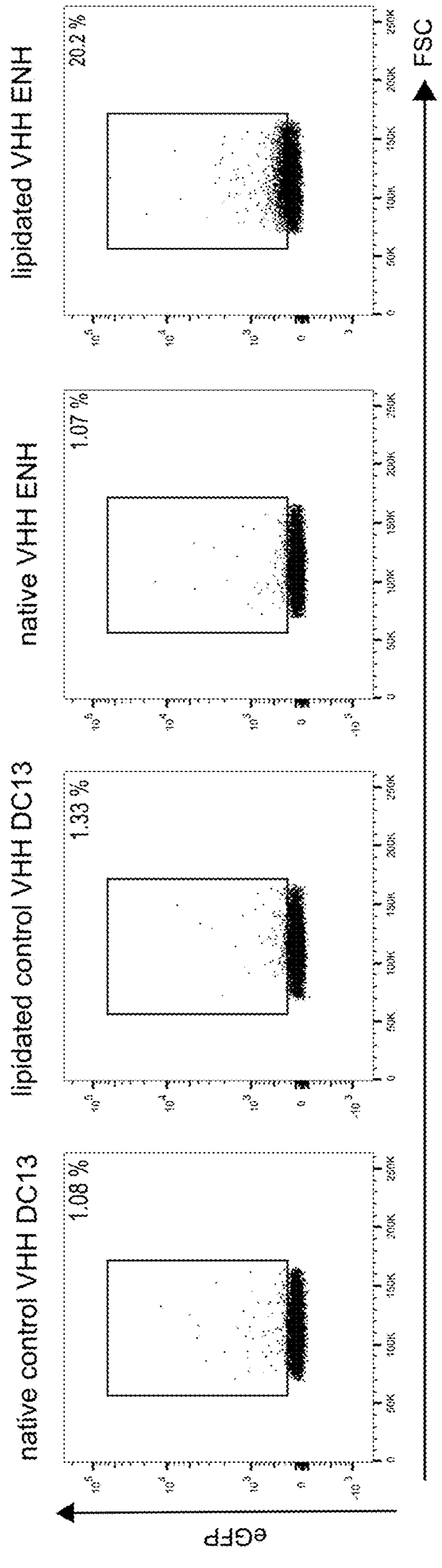
FIG. 11 illustrates flow cytometry revealing a selective capturing of eGFP by cells which had been treated with the lipidated VHH ENH.
Figure 12:
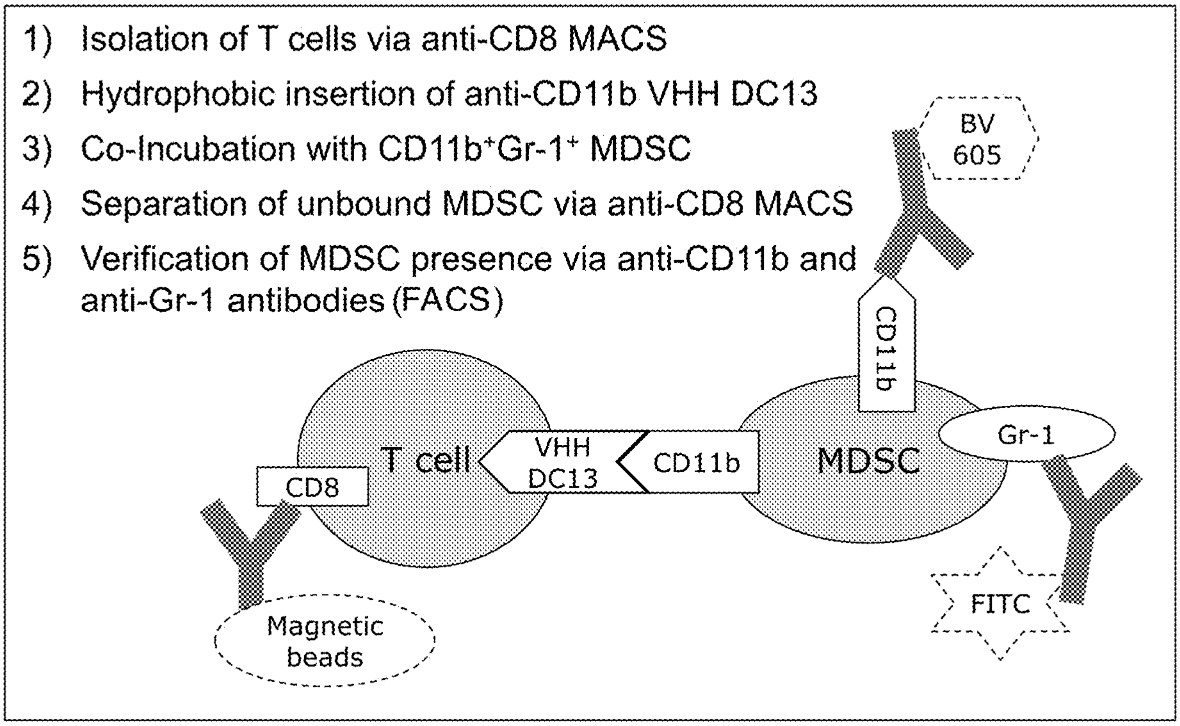
FIG. 12 illustrates CD8+retentate stained for CD11b and Gr-1 and analyzed by flow cytometry.
Figure 13:
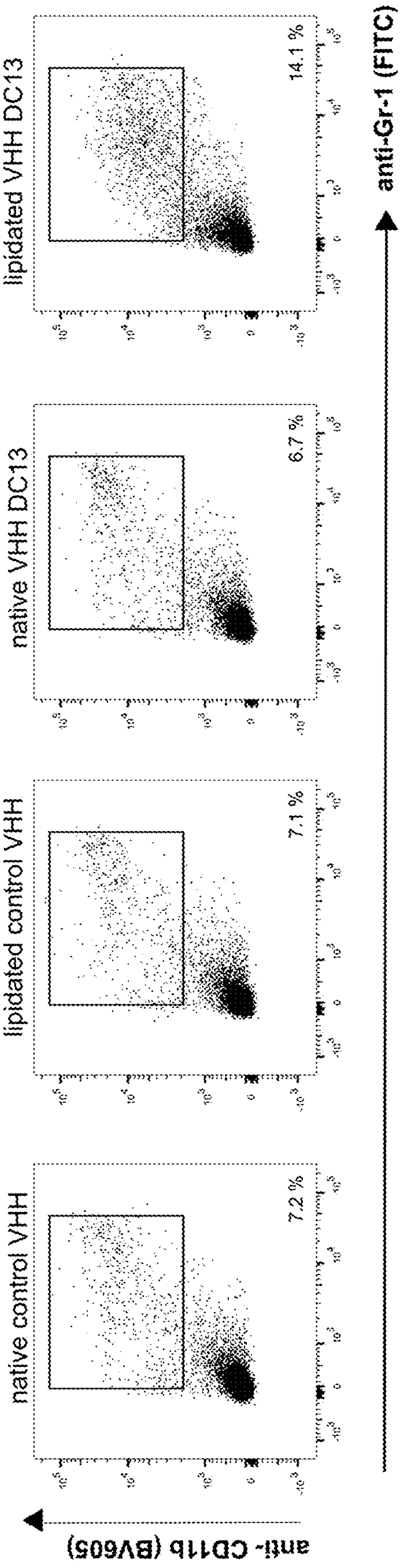
FIG. 13 illustrates that cellular populations pre-incubated with lipidated VHH DC13 caused higher signals for MDSC in the CD8-positive column retentate, indicating a VHH promoted cellular interaction between MDSC and T cells.
Figure 14:
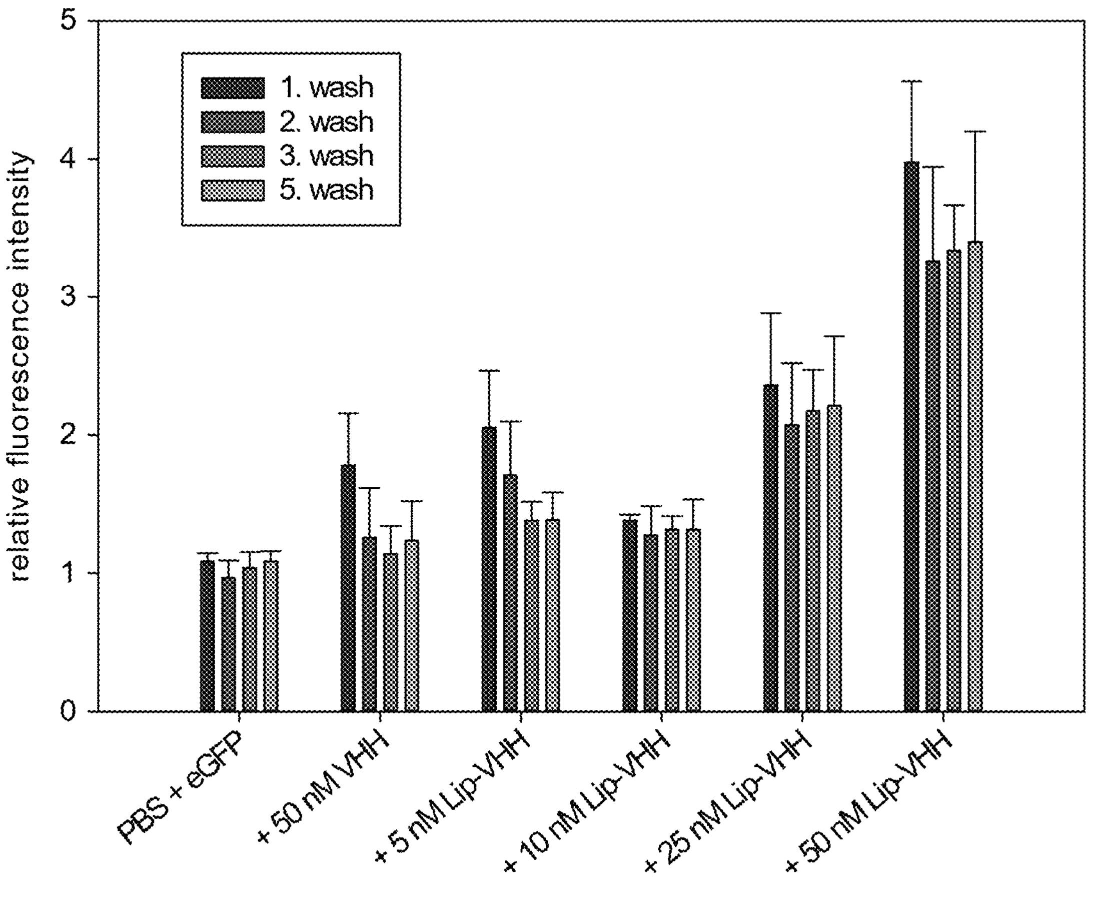
FIG. 14 illustrates that after several washing steps, a significant coating and retention eGFP was observed in the wells for 25 nM and 50 nM coating

```
<160> NUMBER OF SEQ ID NOS: 4

<210> SEQ ID NO 1
<211> LENGTH: 186
<212> TYPE: PRT
<213> ORGANISM: Homo sapiens

<400> SEQUENCE: 1

Met Gly His His His His His His Ser Ser Gly Leu Val Pro Arg Gly
1               5                   10                  15

Ser Gly Met Lys Glu Thr Ala Ala Ala Lys Phe Glu Arg Gln His Met
            20                  25                  30

Asp Ser Pro Asp Leu Gly Thr Gln Ala Lys Pro Gln Ile Pro Lys Asp
        35                  40                  45

Lys Ser Lys Val Ala Gly Tyr Ile Glu Ile Pro Asp Ala Asp Ile Lys
    50                  55                  60

Glu Pro Val Tyr Pro Gly Pro Ala Thr Arg Glu Gln Leu Asn Arg Gly
65                  70                  75                  80

Val Ser Phe Ala Lys Glu Asn Ala Ser Leu Asp Asp Gln Asn Ile Ser
                85                  90                  95

Ile Ala Gly His Thr Phe Ile Asp Arg Pro Asn Tyr Gln Phe Thr Asn
            100                 105                 110

Leu Lys Ala Ala Lys Lys Gly Ser Met Val Tyr Phe Lys Val Gly Asn
        115                 120                 125

Glu Thr Arg Lys Tyr Lys Met Thr Ser Ile Arg Asn Val Lys Pro Thr
    130                 135                 140

Ala Val Glu Val Leu Asp Glu Gln Lys Gly Lys Asp Lys Gln Leu Thr
145                 150                 155                 160

Leu Ile Thr Cys Asp Asp Tyr Asn Glu Glu Thr Gly Val Trp Glu Thr
                165                 170                 175

Arg Lys Ile Phe Val Ala Thr Glu Val Lys
            180                 185


<210> SEQ ID NO 2
<211> LENGTH: 132
<212> TYPE: PRT
<213> ORGANISM: Homo sapiens

<400> SEQUENCE: 2

Gln Val Gln Leu Gln Glu Ser Gly Gly Gly Leu Val Gln Ala Gly Gly
1               5                   10                  15

Ser His Asn Leu Ser Cys Thr Ala Ser Gly Ile Thr Phe Ser Ser Leu
```

```
            20                  25                  30

Ala Met Gly Trp Phe Arg Gln Thr Pro Gly Lys Glu Arg Glu Phe Val
        35                  40                  45

Ala Asn Ile Met Arg Ser Gly Ser Ser Val Phe Tyr Ala Asp Ser Val
    50                  55                  60

Arg Gly Arg Phe Thr Ile Ser Arg Asp Asn Ala Lys Asn Thr Ala His
65                  70                  75                  80

Leu Gln Met Asn Ser Leu Lys Pro Glu Asp Thr Ala Val Tyr Phe Cys
                85                  90                  95

Ala Ala Thr Arg Gly Ala Trp Pro Ala Glu Tyr Trp Gly Gln Gly Thr
            100                 105                 110

Gln Val Thr Val Ser Ser Gly Gly Leu Pro Glu Thr Gly Gly His His
        115                 120                 125

His His His His
    130
```

<210> SEQ ID NO 3
<211> LENGTH: 129
<212> TYPE: PRT
<213> ORGANISM: Homo sapiens

<400> SEQUENCE: 3

```
Gln Val Gln Leu Gln Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser Gly Gly Leu Pro Glu Thr Gly Gly His His His His His
        115                 120                 125

His
```

<210> SEQ ID NO 4
<211> LENGTH: 245
<212> TYPE: PRT
<213> ORGANISM: Aequorea victoria

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80
```

-continued

```
Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys His
225                 230                 235                 240

His His His His His
                245
```

The invention claimed is:

1. A process for the preparation of a conjugate, suitable to be inserted into hydrophobic environments selected from the group consisting of hydrophobic polymeric surfaces, lipid based drug delivery systems and membranes of living cells, wherein the conjugate comprises a biological molecule, an enzymatic tag, a hydrophilic spacer, a linker and a lipophilic moiety, wherein such process comprises enzymatic coupling of a component comprising the enzymatic tag, the hydrophilic spacer, the linker and the lipophilic moiety with the biological molecule in an aqueous medium and wherein such process comprises the following steps:

a) preparing an aqueous dispersion of a component which has the formula (II):

(II)

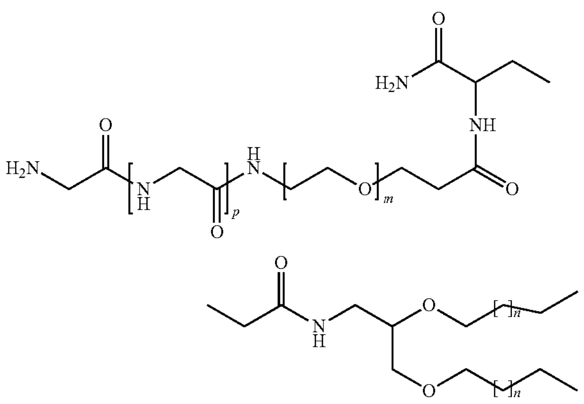

wherein m is any integer number from 15 to 60;

n is any integer number from 3 to 27;

p is any integer number from 0 to 9;

b) adding a transpeptidase and the biological molecule which is a polypeptide selected from an antigen, a cell adhesion protein, a peptide hormone, a cytokine, or a receptor related to any of these molecules, an enzyme, or a natural or artificial antibody or fragment thereof;

c) incubating the mixture obtained in step (b) to produce the conjugate with the biological molecule;

d) purifying the conjugate obtained in step (c).

2. The process according to claim 1, wherein the antibody is a monoclonal antibody or a fragment thereof, such as a single-chain variable fragment (scFv), a variable fragment (Fv), or a fragment antigen binding (Fab, Fab' or F (ab') 2); a camelid or cartilaginous fish-derived heavy-chain only antibody or a fragment thereof, such as a VHH or a vNAR, or wherein the artificial antibody is a DARPin, a adnectine, an anticalin, or an affibody.

3. The process according to claim 1, wherein the biological molecule is a single-domain antibody derived from the variable domain of camelid heavy-chain only antibodies (VHH).

4. The process according to claim 1, wherein the biological molecule prior to its coupling with the component according to formula (II) carries a C-terminal motif for enzymatic conjugation by transpeptidases.

5. The process according to claim 4, wherein the C-terminal motif consists of the amino acid sequence "leucine-proline-X-threonine-glycine" (LPXTG), wherein "X" can be any proteinogenic amino acid.

6. The process according to claim 5, wherein the proteinogenic amino acid present in the LPXTG motif is glycine, alanine, valine, leucine, isoleucine, methionine, phenylalanine, proline, serine, threonine, tyrosine, asparagine, glutamine, aspartic acid, glutamic acid, lysine, arginine or histidine.

7. The process according to claim 1, wherein the component according to formula (II) is (DMA-PEG-G5)

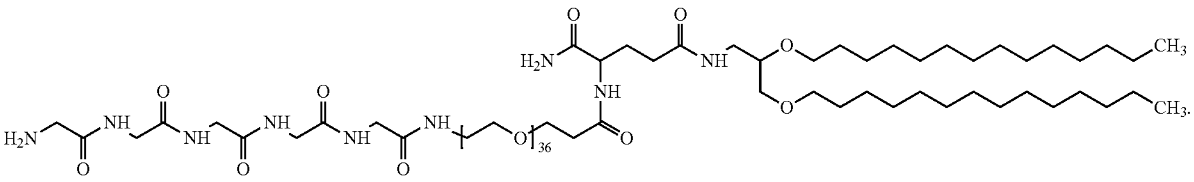

8. The process according to claim 1, wherein the biological molecule is an integrin, a cadherin, a growth factor or an interleukin.

9. The process according to claim 1, wherein m is from 25 to 45.

10. The process according to claim 9, wherein m is from 30 to 40.

11. The process according to claim 10, wherein m is 36.

12. The process according to claim 1, wherein n is from 7 to 19.

13. The process according to claim 12, wherein n is from 11 to 15.

14. The process according to claim 13, wherein n is 11.

15. The process according to claim 1, wherein p is from 2 to 7.

16. The process according to claim 15, wherein p is from 3 to 5.

17. The process according to claim 16, wherein p is 4.

18. The process according to claim 1 wherein the transpeptidase in step (b) is sortase.

19. The process according to claim 18 wherein the sortase is sortase A.

* * * * *